United States Patent
Chang et al.

(10) Patent No.: US 7,557,133 B2
(45) Date of Patent: Jul. 7, 2009

(54) CASPASE INHIBITORS CONTAINING ISOXAZOLINE RING

(75) Inventors: Hye-Kyung Chang, Daejeon (KR); Yeong-Soo Oh, Daejeon (KR); Cheol-Won Park, Daejeon (KR); Yong-Jin Jang, Daejeon (KR); Tae-Kyo Park, Daejeon (KR); Sung-Sub Kim, Daejeon (KR); Min-Jung Kim, Daejeon (KR); Mi-Jeong Park, Daejeon (KR); Jung-Gyu Park, Daejeon (KR); Hee-Dong Park, Daejeon (KR); Kyeong-Sik Min, Daejeon (KR); Tae-Soo Lee, Daejeon (KR); Sang-Kyun Lee, Daejeon (KR); Soo-Hyeon Kim, Daejeon (KR); Hee-Kyung Jeong, Daejeon (KR); Sun-Hwa Lee, Daejeon (KR); Hwa-Dong Kim, Daejeon (KR); Ae-Ri Kim, Daejeon (KR); Ki-Sook Park, Daejeon (KR); Hyun-Ik Shin, Daejeon (KR); Hyeong-Wook Choi, Daejeon (KR); Kyu-Woong Lee, Daejeon (KR); Jae-Hoon Lee, Daejeon (KR); Tae-Ho Heo, Daejeon (KR); Ho-Jun Kim, Daejeon (KR); Tae-Sik Kwon, Daejeon (KR); Jeong Hui Seong, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 459 days.

(21) Appl. No.: 10/568,503

(22) PCT Filed: Aug. 26, 2004

(86) PCT No.: PCT/KR2004/002139

§ 371 (c)(1),
(2), (4) Date: Feb. 16, 2006

(87) PCT Pub. No.: WO2005/021516

PCT Pub. Date: Mar. 10, 2005

(65) Prior Publication Data

US 2006/0223848 A1    Oct. 5, 2006

(30) Foreign Application Priority Data

Aug. 27, 2003   (KR) .................... 10-2003-0059451

(51) Int. Cl.
A61K 31/42   (2006.01)
C07D 261/00  (2006.01)
C07D 261/14  (2006.01)
C07D 261/18  (2006.01)

(52) U.S. Cl. ............... 514/380; 514/378; 548/240; 548/243; 548/244; 548/245; 548/246; 548/248

(58) Field of Classification Search ........... 514/378, 514/380; 548/240, 243, 244, 245, 246, 248
See application file for complete search history.

(56) References Cited

FOREIGN PATENT DOCUMENTS

| KR | 1999-0079268 A | 11/1999 |
|----|----------------|---------|
| WO | WO-94/12481 A1 | 6/1994 |
| WO | WO-95/14680 A1 | 6/1995 |
| WO | WO-95-14681 A1 | 6/1995 |
| WO | WO 01/21599 * | 3/2001 |
| WO | WO-01/21600 A1 | 3/2001 |

OTHER PUBLICATIONS

"Dementia" Retrieved online via Internet: Jun. 10, 2008-URL: www.nlm.nih.gov/medlineplus/dementia.html#cat5.*
Gripenberg, M, Scand. J. Rheumatology, vol. 10 (2) 1981, 85-91.*

* cited by examiner

*Primary Examiner*—Kamal A Saeed
*Assistant Examiner*—Samantha L Shterengarts
(74) *Attorney, Agent, or Firm*—Birch, Stewart, Kolasch & Birch, LLP

(57) ABSTRACT

The present invention relates to an isoxazoline derivative as an inhibitor against various caspases, a process for preparing the same, and a therapeutic composition for preventing inflammation and apoptosis comprising the same.

21 Claims, 2 Drawing Sheets

[Fig. 1]
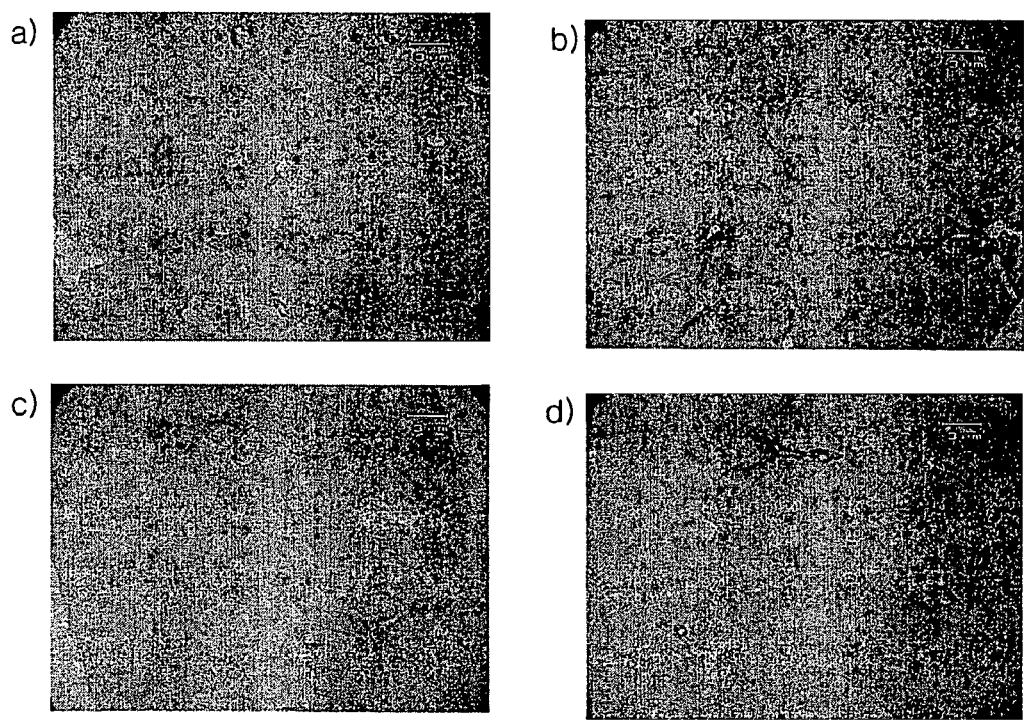

[Fig. 2]
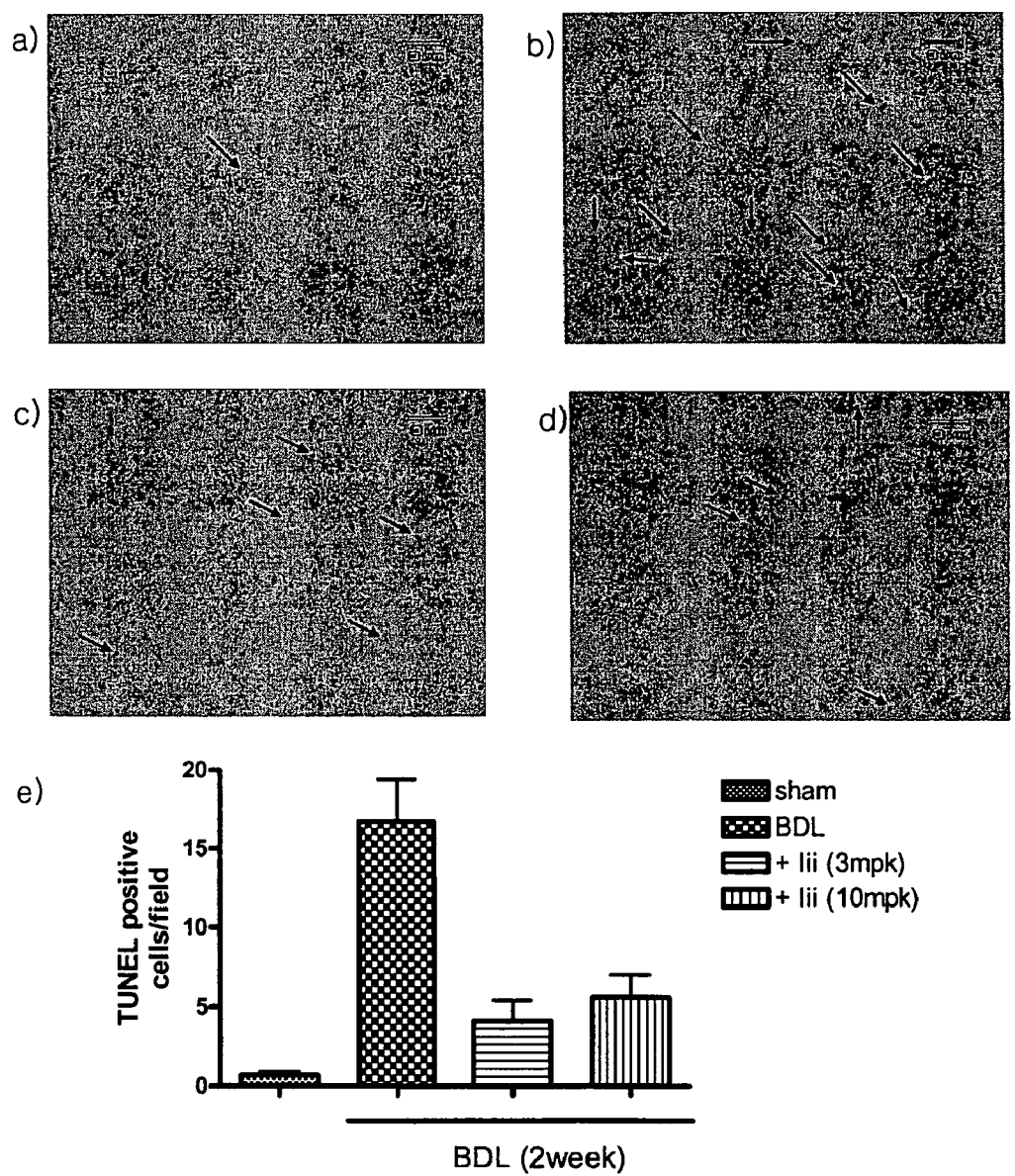

CASPASE INHIBITORS CONTAINING ISOXAZOLINE RING

TECHNICAL FIELD

The present invention relates to an isoxazoline derivative as an inhibitor against various caspases including caspase-1[interleukin-1β converting enzyme, ICE] and caspase-3[apopain/CPP-32], a process for preparing the same, and a therapeutic composition for preventing inflammation and apoptosis comprising the same.

BACKGROUND ART

Caspase is a new kind of cysteine protease in the form of $\alpha_2\beta_2$ discovered during the last 10 years. About 14 kinds thereof have been known until now. Caspase-1(ICE), one of them, is a kind of cytokines and participates in converting the inactive prointerleukin-1β to the active interleukin-1β. Interleukin-1 consists of interleukin-1α and interleukin-1, both of which are synthesized in monocytes in the form of a precursor having 31 kDa. Only prointerleukin-1β is activated by ICE. The positions hydrolyzed by caspase-1 are $Asp^{27}$-$Gly^{28}$ and $Asp^{116}$-$Ala^{117}$. The hydrolysis of the latter position gives interleukin-1β. Interleukin-1β has been reported to act as an important mediator in causing inflammation (1,3). Caspase-1 has been discovered for the first time in 1989, and in two independent study groups, the three dimensional structure thereof was determined by X-ray crystallographic method.

Caspase-3(CPP-32) is broadly studied for its role or mechanism for action, and its three dimensional structure was determined in 1996(2). Caspase-3(apopain) activated from procaspase-3 hydrolyzes (P4)Asp-X-X-Asp(P1) motif, and the known substrates include poly(ADP-ribose) polymerase, U1 70,000 Mr small nuclear ribonucleoprotein and catalytic subunit of 460,000 Mr DNA-dependent protein kinase, etc. The X-ray structure of caspase-7 has been reported to be very similar to that of caspase-3(4).

Caspase-8 and 9 are present in the upstream of caspase-3, 6,7, and these caspases are known to participate in the apoptosis cascade. The X-ray structure of caspase-8 was determined in 1999(5), and particularly the inhibitors thereof may be advantageously used for treating the diseases related to apoptosis.

Caspase inhibitors mean those compounds that inhibit the activity of caspase, and so control such symptoms as inflammation, apoptosis, etc. caused by the caspase activity. Diseases or symptoms that may be treated or attenuated by administering the inhibitors include the following: rheumatoid arthritis, inflammatory bowel disease, graft vs. host disease, sepsis, osteoarthritis, osteoporosis, acute and chronic myelogenous leukemia, meningitis, salpingitis, septic shock, cholangitis, colitis, encephalitis, endocarditis, glomerulonephritis, hepatitis, myocarditis, pancreatitis, type I diabetes mellitus, multiple sclerosis, Alzheimer's disease, Parkinson's disease, hepatocirrhosis (6).

Among the caspase inhibitors known until now, the most noted irreversible inhibitors are the following:

IDN-1965

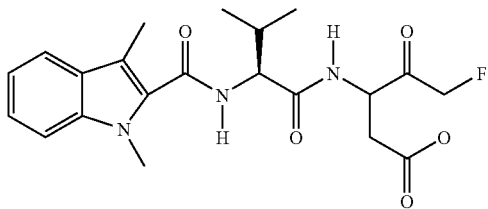

-continued

MX-1013

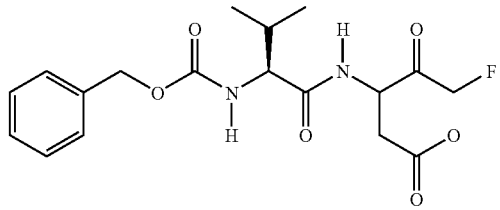

Both the above inhibitors exhibit their activity based on the common mechanism that they irreversibly inactivate the enzyme to suppress the cell apoptosis (irreversible, broad-spectrum inhibitor). It has been reported that irreversible inhibitor has much more effective inhibitory activity when comparing the irreversible and reversible inhibitors (7). Both IDN-1965 of IDUN Co. and MX-1013 of Maxim Co. are reported to show activity in cell apoptosis model for hepatic injury (8, 9). These compounds are now in the stage of pre-clinical test. The irreversible inhibitor IDN-6556, the structure of which has been recently reported, is now in the stage of phase II clinical test as a therapeutic agent for hepatic injury (10, 11).

IDN-6556

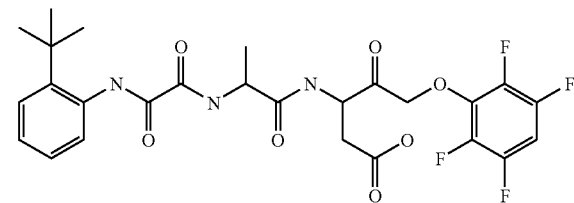

REFERENCES (1) *Inflammation: Basic Principles and Clinical Correlates*, 2nd ed., ed by Gallin, Goldstein and Snyderman. Raven Press Ltd., New York. 1992, pp 211-232; *Blood*, 1996, 87(6), 2095-2147.

(2) Wilson, K. P. et al, *Nature*, 1994, 370. 270; Walker, N. P. C. et al. *Cell*, 1994, 78, 343; Nature Structural Biology, 1996, 3(7), 619.

(3) Thornberry, N. A. et al, *Nature*, 1992, 356. 768; *Nature Biotechnology*, 1996, 14, 297; *Protein Science*, 1995, 4, 3; *Nature*, 1995, 376(July 6), 37; *Protein Science*, 1995, 4, 2149.

(4) Wei, Y. et al, *Chemistry and Biology*, 2000, 7, 423.

(5) Blanchard H. et al, *Structure*, 1999, 7, 1125; Blanchard H. et al, *J. of Mol. Biol.*, 2000, 302, 9.

(6) References for caspase related diseases

Dementia: Arch Neurol 2003 March; 60(3):369-76, Caspase gene expression in the brain as a function of the clinical progression of Alzheimer disease. Pompl P N, Yemul S, Xiang Z, Ho L, Haroutunian V, Purohit D, Mohs R, Pasinetti G M.

Cerebral stroke: Proc Natl Acad Sci USA 2002 Nov. 12; 99(23):15188-93, Caspase activation and neuroprotection in caspase-3-deficient mice after in vivo cerebral ischemia and in vitro oxygen glucose deprivation. Le D A, Wu Y, Huang Z, Matsushita K, Plesnila N, Augustinack J C, Hyman B T, Yuan J, Kuida K, Flavell R A, Moskowitz M A.

Brain impairment due to AIDS: J Neurosci 2002 May 15; 22(10):4015-24, Caspase cascades in human immunodeficiency virus-associated neurodegeneration. Garden G A, Budd S L, Tsai E, Hanson L, Kaul M, D'Emilia D M, Friedlander R M, Yuan J, Masliah E, Lipton S A.

Diabetes: Diabetes 2002 June; 51(6):1938-48, Hyperglycemia-induced apoptosis in mouse myocardium: mitochondrial cytochrome C-mediated caspase-3 activation pathway. Cai L, Li W, Wang G, Guo L, Jiang Y, Kang Y J.

Gastric ulcer: J Physiol Pharmacol 1998 December; 49(4): 489-500, Role of basic fibroblast growth factor in the suppression of apoptotic caspase-3 during chronic gastric ulcer healing. Slomiany B L, Piotrowski J, Slomiany A.

Cerebral injure by hepatitis: J Viral Hepat 2003 March; 10(2): 81-6, Cerebral dysfunction in chronic hepatitis C infection. Forton D M, Taylor-Robinson S D, Thomas H C.

Fulminant hepatic failure: Gastroenterology 2000 August; 119(2):446-60, Tumor necrosis factor alpha in the pathogenesis of human and murine fulminant hepatic failure. Streetz K, Leifeld L, Grundmann D, Ramakers J, Eckert K, Spengler U, Brenner D, Manns M, Trautwein C.

Sepsis: Nat Immunol 2000 December; 1(6):496-501, Caspase inhibitors improve survival in sepsis: a critical role of the lymphocyte. Hotchkiss R S, Chang K C, Swanson P E, Tinsley K W, Hui J J, Klender P, Xanthoudakis S, Roy S, Black C, Grimm E, Aspiotis R, Han Y, Nicholson D W, Karl I E.

Organ transplantation rejection: Xenotransplantation 2001 May; 8(2):115-24, In vitro prevention of cell-mediated xeno-graft rejection via the Fas/FasL-pathway in CrmA-transducted porcine kidney cells. Fujino M, Li X K, Suda T, Hashimoto M, Okabe K, Yaginuma H, Mikoshiba K, Guo L, Okuyama T, Enosawa S, Amemiya H, Amano T, Suzuki S.

Rheumatic arthritis: Prog Med Chem 2002; 39:1-72, Caspase inhibitors as anti-inflammatory and antiapoptotic agents. Graczyk P P.

Ischemic cardiac diseases: Am J Physiol Heart Circ Physiol 2002 September; 283(3):H990-5, Hypoxia-induced cleavage of caspase-3 and DFF45/ICAD in human failed cardiomyocytes. Todor A, Sharov V G, Tanhehco E J, Silverman N, Bernabei A, Sabbah H N.

Anti-inflammation: J Immunol 2003 Mar. 15; 170(6):3386-91, A broad-spectrum caspase inhibitor attenuates allergic airway inflammation in murine asthma model. Iwata A, Nishio K, Winn R K, Chi E Y, Henderson W R Jr, Harlan J M.

Cirrhosis: i) J Pharmacol Exp Ther. 2004 March; 308(3): 1191-6, The caspase inhibitor Idn-6556 attenuates hepatic injury and fibrosis in the bile duct ligated mouse. Canbay A., Fledstein A., Baskin-Bey E., Bronk F S. Gores G J.; ii) Hepatology. 2004 February; 39(2):273-8, Apoptosis: the nexus of liver injury and fibrosis. Canbay A, Friedman S, Gores G J.; iii) Hepatology. 2003 November; 38(5):1188-98, Kupffer cell engulfment of apoptotic bodies stimulates death ligand and cytokine expression. Canbay A, Feldstein A E, Higuchi H, Werneburg N, Grambihler A, Bronk S F, Gores G J.

(7) Wu J. et al, Methods: *A Companion to Methods in Enzymology*, 1999, 17, 320.

(8) Hoglen N. C. et al, *J. of Pharmacoloy and Experimental Therapeutics*, 2001, 297, 811.

(9) Jaeschke H. et al, *Toxicology and Applied Pharmacology*, 2000, 169, 77.

(10) Hoglen N. C. et al, *J. Pharmacol Exp. Ther.*, 2004, 309(2):634. Characterization of IDN-6556 (3-[2-(2-tert-butyl-phenylaminooxalyl)-amino]-propionylamino]-4-oxo-5-(2,3,5,6-tetrafluoro-phenoxy)-pentanoic acid): a liver-targeted caspase inhibitor;

(11) Canbay A et al, *J. Pharmacol. Exp. Ther.*, 2004, 308(3), 1191. The caspase inhibitor IDN-6556 attenuates hepatic injury and fibrosis in the bile duct ligated mouse.

DISCLOSURE OF THE INVENTION

The present inventors newly designed and synthesized some compounds which can be used as an effective inhibitor against caspases and have a distinctive structure and high selectivity for similar enzymes, and determined their binding ability and inhibitory activity for caspases. As a result, the inventors have discovered that a compound of the following formula (1) does meet such requirements, and completed the present invention.

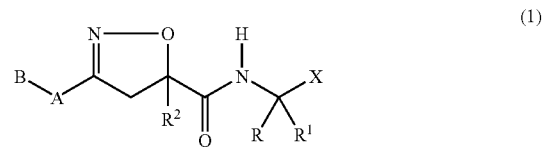

(1)

in which

A, B, R, $R^1$, $R^2$ and X are defined as described below.

Therefore, the present invention provides the novel isoxazoline derivative of formula (1), salt, or stereoisomer thereof having effective inhibitory activity against caspases.

It is another object of the present invention to provide a process for preparing the compound of formula (1), salt, or stereoisomer thereof.

It is also another object of the present invention to provide a composition, a use, or a method for inhibiting caspases, specifically a therapeutic composition, a use, or a method for preventing inflammation and apoptosis, comprising the compound of formula (1), salt, or stereoisomer thereof as an active ingredient together with the pharmaceutically acceptable carrier.

BRIEF DESCRIPTION OF THE DRAWINGS

FIG. 1 shows the inhibitory activity of Compound (Iii) against the hepatic fibrosis due to the bile stagnation: "a)" in FIG. 1 represents the case of Sham operation, "b)" represents the case of BDL operation where only the vehicle was administered after the ligation of biliary duct, "c)" represents the case where Compound (Iii) was orally administered in a dosage of 3 mg/kg twice a day for 1 week after 1 week from the ligation of biliary duct, and "d)" represents the case where Compound (Iii) was orally administered in a dosage of 10 mg/kg twice a day for 1 week after 1 week from the ligation of biliary duct.

FIG. 2 shows the inhibitory activity of Compound (Iii) against the hepatic cell apoptosis due to the bile stagnation: "a)" in FIG. 2 represents the case of Sham operation, "b)" represents the case of BDL operation where only the vehicle was administered after the ligation of biliary duct, "c)" represents the case where Compound (Iii) was orally administered in a dosage of 3 mg/kg twice a day for 1 week after 1 week from the ligation of biliary duct, "d)" represents the case where Compound (Iii) was orally administered in a dosage of 10 mg/kg twice a day for 1 week after 1 week from the ligation of biliary duct, and "e)" is a graph showing the number of hepatic cells subjected to apoptosis in each treatment group.

BEST MODE FOR CARRYING OUT THE INVENTION

In advance of illustrating the present invention in detail, the following important terms are defined first:

a) Simple Alkyl Chain (SAC, below) means a hydrocarbon having 1 to 8 carbon atoms in either linear or branched isomeric form.

b) Simple CycloAlkyl Chain (SCAC, below) means a cyclic radical having 3 to 10 carbon atoms.

c) Aryl group (Ar, below) includes both the aromatic and heteroaromatic groups. The aromatic group means a 5 to 15-membered single or fused unsaturated cycle. One or more hydrogens may be replaced with a group(s) selected from the following: acyl, amino, carboalkoxy, carboxy, carboxyamino, cyano, halo, hydroxy, nitro, thiol, alkyl, cycloalkyl, alkoxy, aryloxy, sulfoxy, and guanido group. The heteroaromatic group means the aromatic group containing 1 to 5 hetero atoms selected from a group consisting of oxygen, sulfur, and nitrogen. Likewise, one or more hydrogens may be replaced with a group(s) selected from the following: acyl, amino, carboalkoxy, carboxy, carboxyamino, cyano, halo, hydroxy, nitro, thiol, alkyl, cycloalkyl, alkoxy, aryl, aryloxy, sulfoxy, and guanido group. Or, for example, in the case of pyridyl, an alkyl group can be added to the nitrogen atom to convert the pyridyl group to a pyridinium group having (+)-charge on the nitrogen atom.

The aryl group includes phenyl, biphenyl, 1-naphthyl, 2-naphthyl, pyridinyl, N-alkyl-pyridinium, pyrimidinyl, quinolinyl, benzothienyl, indolyl, pyrazinyl, isoindolyl, isoquinolyl, qunazolinyl, quinoxalinyl, phthalazinyl, imidazolinyl, isoxazolyl, pyrazolyl, oxazolyl, thiazolyl, indolizinyl, indazolyl, benzothiazolyl, benzimidazolyl, benzofuranyl, thienyl, pyrrolyl, oxadiazolyl, thiadiazolyl, triazolyl, tetrazolyl, oxazolopyridinyl, imidazopyridinyl, isothiazolyl, cinnolinyl, carbazolyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiopyranyl, benzopyranyl, benzothiopyranyl, coumarinyl, isocoumarinyl, chromonyl, chromanonyl, pyridinyl-N-oxide, tetrahydroquinolinyl-N-oxide, dihydroquinolinyl, dihydroquinolinonyl, dihydroisoquinolinonyl, dihydrocoumarinyl, dihydroisocoumarinyl, isoindolinonyl, benzodioxanyl), benzoxazolinonyl, N-alkylpyridium, pyrrolyl-N-oxide, pyrimidinyl-N-oxide, pyrazinyl-N-oxide, quinolinyl-N-oxide, indolyl-N-oxide, indolinyl-N-oxide, isoquinolyl-N-oxide, qunazolinyl-N-oxide, quinoxalinyl-N-oxide, phthalazinyl-N-oxide, imidazolinyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, etc.

d) Simple Alkyl Chain substituted by Aryl (SAC-Ar, below) means a straight-chain or branched alkyl which has 1 to 8 carbon atoms and is substituted by the above mentioned aryl group.

e) Natural amino acid includes the following: Glycine, Alanine, Valine, Leucine, Isoleucine, Serine, Threonine, Cysteine, Methionine, Proline, Aspartic acid, Asparagine, Glutamic acid, Glutamine, Lysine, Arginine, Histidine, Phenylalanine, Tyrosine, and Tryptophan f) The protecting group of simple ester is a hydrocarbon having 1 to 8 carbon atoms in either linear or branched isomeric form.

Further, the present specification includes the following abbreviations:

N-chlorosuccinimide: NCS
N-methylmorpholine: NMM
O-(7-azabenzotriazol-1-yl)-N,N,N',N'-tetramethyluroniumhexafluorophosphate: HATU
N,N-dimethyl formamide: DMF
1-(3-dimethylaminopropyl)-3-ethylcarbodiimide: EDC
1-hydroxybenzotriazole hydrate: HOBt
trifluoroacetic acid: TFA
t-butoxycarbonyl: Boc
benzyloxycarbonyl: Cbz
methyl: Me
ethyl: Et
equivalent: Eq The substituents included in the above formula (1) are specifically defined as follows.

I) R represents H, simple alkyl chain (-SAC), simple cycloalkyl chain (-SCAC), aryl group (—Ar), or simple alkyl chain substituted by aryl (-SAC-Ar), II) $R^1$ represents -SAC, -SCAC, —Ar, -SAC-Ar, or a side chain residue of all the natural amino acids; and the compound of formula (1) may exist in a specific diastereomeric form, or mixtures thereof when the carbon to which $R^1$ is attached becomes a stereocenter due to the $R^1$ group; or the compound of formula (1) may have a protecting group in an ester form (—$CO_2R^3$ wherein $R^3$ is -SAC) or a sulfonamide form (—$CONHSO_2R^4$ wherein $R^4$ is -SAC), or may exist in the form of pharmaceutically acceptable salt, when $R^1$ is a side chain residue of an amino acid containing carboxyl moiety; or the compound of formula (1) may also exist in the form of pharmaceutically acceptable salt when $R^1$ is a side chain residue of an amino acid containing a base moiety, III) $R^2$ represents -SAC, -SCAC, —Ar, -SAC-Ar, or a side chain residue of the natural amino acids; and the compound of formula (1) may exist in a specific diastereomeric form, or mixtures thereof when the carbon to which $R^2$ is attached becomes a stereocenter due to the $R^2$ group; the compound of formula (1) may have a protecting group in an ester form (—$CO_2R^5$ wherein $R^5$ is -SAC) or a sulfonamide form (—$CONHSO_2R^6$ wherein $R^6$ is -SAC), or may exist in the form of pharmaceutically acceptable salt, when $R^2$ is a side chain residue of an amino acid containing carboxyl moiety; or the compound of formula (1) may also exist in the form of pharmaceutically acceptable salt when $R^2$ is a side chain residue of an amino acid containing a base moiety, or $R^2$ further represents H; —$(CH_2)_n OR^7$ wherein $R^7$ is -SAC, -SCAC, —Ar, or -SAC-Ar, and n=1 or 2; or —$(CH_2)_n OC(=O)R^8$ wherein $R^8$ is -SAC, -SCAC, —Ar, or -SAC-Ar, and n=1 or 2, IV) A represents —$(CH_2)_n$— (n=0-4), —O—$(CH_2)_n$— (n=0-4), or —$NR^9$—$(CH_2)_n$— (n=0-4) wherein $R^9$ is -SAC, -SCAC, —Ar, or -SAC-Ar, V) B represents H, -SAC, -SCAC, —Ar, or -SAC-Ar, or VI) R and $R^1$ may form a cycle together with the carbon atom to which they are attached, where —R—$R^1$— is —$(CH_2)_n$—, —$(CH_2)_n$—O—$(CH_2)_m$—, or —$(CH_2)_n$—$NR^{10}$—$(CH_2)_m$— wherein n+m<9 and $R^{10}$ is -SAC, -SCAC, —Ar, -SAC-Ar, —C(=O)-SAC, —C(=O)-SCAC, —C(=O)—Ar, or —C(=O)-SAC-Ar, VII) X represents —C(=O)CH$_2$OR$^{11}$ wherein R$^{11}$ is -SAC, -SCAC, —Ar, or -SAC-Ar; —C(=O)CH$_2$C(=O)R$^{12}$ wherein R$^{12}$ is -SAC, -SCAC, —Ar, or -SAC-Ar; —CH=CH—CO$_2$R$^{13}$ wherein R$^{13}$ is -SAC, -SCAC, —Ar, or -SAC-Ar; —CH=CH—SO$_2$R$^{14}$ wherein R$^{14}$ is -SAC, -SCAC, —Ar, or -SAC-Ar; —C(=O)CH=CH$_2$; or —COCH$_2$—W wherein W is —N$_2$, —F, —Cl, —Br, —I, —NR$^{15}$R$^{16}$ (R$^{15}$ and R$^{16}$ each are —SAC, -SCAC, —Ar, or -SAC-Ar, or together may form 3- to 6-membered saturated or unsaturated cyclic group), —SR$^{17}$ (R$^{17}$ is -SAC, -SCAC, —Ar, or -SAC-Ar), or is the following formula:

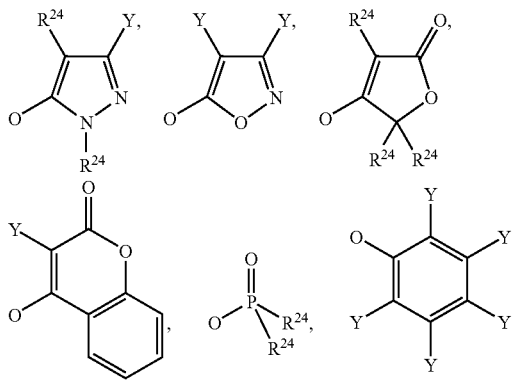

wherein
Y is H, —OH, —OR$^{18}$ (R$^{18}$=-SAC or -SCAC), —C(=O)R$^{19}$ (R$^{19}$=—H, -SAC, or -SCAC), —F, —Cl, —Br, —I, —CN, —NC, —N$_3$, —CO$_2$H, CF$_3$, —CO$_2$R$^2$ (R$^{20}$=-SAC or -SCAC), —C(=O)NHR$^{21}$ (R$^{21}$=-SAC or -SCAC), or —C(=O)NR$^{22}$R$^{21}$ (R$^{22}$ and R$^{23}$ each are -SAC, -SCAC, —Ar, or -SAC-Ar), R$^{21}$ is H, -SAC, -SAC-Ar, or —Ar.

The preferred compounds among the compound of formula (1) above are those wherein
R represents H;
R$^1$ represents —CH$_2$COOH, —CH$_2$COOR$^3$ (R$^3$=SAC), or —CH$_2$CONHSO$_2$R$^4$ (R$^4$=SAC);
R$^2$ represents H, -SAC, —Ar, or —(CH$_2$)$_n$OR$^7$ (R$^7$=-SAC, -SCAC, —Ar, or -SAC-Ar, and n=1 or 2); or
X represents —C(=O)CH$_2$OAr, —C(=O)CH$_2$C(=O)Ar, or —COCH$_2$—W wherein W is —N$_2$, —F, —Cl, —Br, —I, —NR$^{15}$R$^{16}$ (R$^1$5 and R$^{16}$ each are -SAC, -SCAC, —Ar, or -SAC-Ar, or together may form 3- to 6-membered saturated or unsaturated cyclic group), or —SR$^{17}$ (R$^{17}$ is -SAC, -SCAC, —Ar, or -SAC-Ar).

More preferred compounds among the compound of formula (1) above are those wherein
I) R represents H,
II) R$^1$ represents —CH$_2$COOH, —CH$_2$COOR$^3$ (R$^3$=SAC), or —CH$_2$CONHSO$_2$R$^4$ (R$^4$=SAC),
III) R$^2$ represents H, -SAC, —Ar, or —(CH$_2$)$_n$OR$^7$ (R$^7$=-SAC, -SCAC, —Ar, or -SAC-Ar, and n=1 or 2),
IV) A represents —(CH$_2$)$_n$— (n=0-4) or —O—(CH$_2$)$_n$— (n=0-4),
V) B represents H, -SAC, -SCAC, —Ar, or -SAC-Ar,
VI) X represents —COCH$_2$N$_2$, —COCH$_2$F, —COCH$_2$Cl, —COCH$_2$Br, —COCH$_2$I, —COCH$_2$OAr, —COCH$_2$OCOAr, or —COCH$_2$SR$^{17}$ (R$^{17}$ is -SAC, -SCAC, —Ar or -SAC-Ar).

Particularly preferred compounds are those selected from the following group:

(1) (3S)-5-[(2,6-dichlorobenzoyl)oxy]-3-({[5-methyl-3-phenyl-4,5-dihydro-5-isoxazolyl]carbonyl}amino)-4-oxopentanoic acid (Iaa);
(2) (3S)-3-({[5-methyl-3-phenyl-4,5-dihydro-5-isoxazolyl]carbonyl}amino)-4-oxo-5-phenoxypentanoic acid (Ibb);
(3) (3S)-3-({[5-ethyl-3-phenyl-4,5-dihydro-5-isoxazolyl]carbonyl}amino)-4-oxo-5-(2,3,5,6-tetrafluorophenoxy)pentanoic acid (Icc);
(4) (3S)-3-({[5-ethyl-3-(1-naphthyl)-4,5-dihydro-5-isoxazolyl]carbonyl}amino)-4-oxo-5-(2,3,5,6-tetrafluorophenoxy)pentanoic acid (Idd);
(5) (3S)-3-({[5-ethyl-3-(2-naphthyl)-4,5-dihydro-5-isoxazolyl]carbonyl}amino)-4-oxo-5-(2,3,5,6-tetrafluorophenoxy)pentanoic acid (Iee);
(6) (3S)-3-({[5-ethyl-3-(1-isoquinolinyl)-4,5-dihydro-5-isoxazolyl]carbonyl}amino)-4-oxo-5-(2,3,5,6-tetrafluorophenoxy)pentanoic acid (Iff);
(7) 3-({[5-ethyl-3-(1-isoquinolinyl)-4,5-dihydro-5-isoxazolyl]carbonyl}amino)-5-fluoro-4-oxopentanoic acid (Igg);
(8) ethyl 3-({[5-ethyl-3-(1-isoquinolinyl)-4,5-dihydro-5-isoxazolyl]carbonyl}amino)-5-fluoro-4-oxopentanoate (Ihh);
(9) 5-fluoro-3-({[(5R)-5-isopropyl-3-(1-isoquinolinyl)-4,5-dihydro-5-isoxazolyl]carbonyl}amino)-4-oxopentanoic acid (Iii);
(10) 3-({[5-ethyl-3-(4-quinolinyl)-4,5-dihydro-5-isoxazolyl]carbonyl}amino)-5-fluoro-4-oxopentanoic acid (Ijj);
(11) 3-({[3-(benzothiophen-2-yl)-5-ethyl-4,5-dihydro-5-isoxazolyl]carbonyl}amino)-5-fluoro-4-oxopentanoic acid (Ikk);
(12) (3S)-3-({[3-(1,3-dimethyl-1H-indol-2-yl)-5-ethyl-4,5-dihydro-5-isoxazolyl]carbonyl}amino)-4-oxo-5-(2,3,5,6-tetrafluorophenoxy)pentanoic acid (Ill);
(13) 3-({[3-(1,3-dimethyl-1H-indol-2-yl)-5-ethyl-4,5-dihydro-5-isoxazolyl]carbonyl}amino)-5-fluoro-4-oxopentanoic acid (1 mm);
(14) (3S)-3-({[5-ethyl-3-(1-naphthylmethyl)-4,5-dihydro-5-isoxazolyl]carbonyl}amino)-4-oxo-5-(2,3,5,6-tetrafluorophenoxy)pentanoic acid (Inn);
(15) (3S)-5-[(2,6-dichlorobenzoyl)oxy]-3-[({5-ethyl-3-[2-(1-naphthyl)ethyl]-4,5-dihydro-5-isoxazolyl}carbonyl)amino]-4-oxopentanoic acid (Ioo);
(16) (3S)-3-[({5-ethyl-3-[(1-naphthyloxy)methyl]-4,5-dihydro-5-isoxazolyl}carbonyl)amino]-4-oxo-5-(2,3,5,6-tetrafluorophenoxy)pentanoic acid (Ipp);
(17) (3S)-3-{[(3-{[(4-chloro-1-naphthyl)oxy]methyl}-5-ethyl-4,5-dihydro-5-isoxazolyl)carbonyl]amino}-4-oxo-5-(2,3,5,6-tetrafluorophenoxy)pentanoic acid (Iqq);
(18) (3S,4E)-6-ethoxy-3-({[(5R)-5-isopropyl-3-(1-isoquinolinyl)-4,5-dihydro-5-isoxazolyl]carbonyl}amino)-6-oxo-4-hexenoic acid (Irr);
(19) (3S,4E)-3-({[(5R)-5-isopropyl-3-(1-isoquinolinyl)-4,5-dihydro-5-isoxazolyl]carbonyl}amino)-5-(methylsulfonyl)-4-pentenoic acid (Iss);
(20) 5-fluoro-3-({[(5S)-3-(1-isoquinolinyl)-5-propyl-4,5-dihydro-5-isoxazolyl]carbonyl}amino)-4-oxopentanoic acid (Itt);
(21) 3-({[(5S)-5-ethyl-3-(-naphthyl)-4,5-dihydro-5-isoxazolyl]carbonyl}amino)-5-fluoro-4-oxopentanoic acid (Iuu);
(22) 3-({[(5S)-5-ethyl-3-(2-quinolinyl)-4,5-dihydro-5-isoxazolyl]carbonyl}amino)-5-fluoro-4-oxopentanoic acid (Ivv);

(23) 3-({[(5R)-5-ethyl-3-(3-isoquinolinyl)-4,5-dihydro-5-isoxazolyl]carbonyl}amino)-5-fluoro-4-oxopentanoic acid (Iww);
(24) 3-({[5-ethyl-3-(8-quinolinyl)-4,5-dihydro-5-isoxazolyl]carbonyl}amino)-5-fluoro-4-oxopentanoic acid (Ixx);
(25) 3-({[5-ethyl-3-(3-quinolinyl)-4,5-dihydro-5-isoxazolyl]carbonyl}amino)-5-fluoro-4-oxopentanoic acid (Iyy);
(26) 5-fluoro-3-({[(5R)-5-isopropyl-3-(2-quinolinyl)-4,5-dihydro-5-isoxazolyl]carbonyl}amino)-4-oxopentanoic acid (Izz);
(27) 3-({[5-ethyl-3-(2-isopropylphenyl)-4,5-dihydro-5-isoxazolyl]carbonyl}amino)-5-fluoro-4-oxopentanoic acid (Iaa1);
(28) 3-[({3-[3-(tert-butyl)phenyl]-5-ethyl]-4,5-dihydro-5-isoxazolyl}carbonyl)amino]-5-fluoro-4-oxopentanoic acid (Iaa2);
(29) 3-[({3-[4-(tert-butyl)phenyl]-5-ethyl-4,5-dihydro-5-isoxazolyl}carbonyl)amino]-5-fluoro-4-oxopentanoic acid (Iaa3);
(30) 5-fluoro-3-({[(5R)-5-isopropyl-3-(2-isopropylphenyl)-4,5-dihydro-5-isoxazolyl]carbonyl}amino)-4-oxopentanoic acid (Iaa4);
(31) 3-[({(5R)-3-[3-(tert-butyl)phenyl]-5-isopropyl-4,5-dihydro-5-isoxazolyl}carbonyl)amino]-5-fluoro-4-oxopentanoic acid (Iaa5);
(32) 3-{[(3-[1,1'-biphenyl]-3-yl-5-isopropyl-4,5-dihydro-5-isoxazolyl)carbonyl]amino}-5-fluoro-4-oxopentanoic acid (Iaa6);
(33) 3-({[5-ethyl-3-(2-pyridinyl)-4,5-dihydro-5-isoxazolyl]carbonyl}amino)-5-fluoro-4-oxopentanoic acid (Iaa7);
(34) 3-[({3-[4-(tert-butyl)-2-pyridinyl]-5-ethyl-4,5-dihydro-5-isoxazolyl}carbonyl)amino]-5-fluoro-4-oxopentanoic acid (Iaa8);
(35) 3-[({(5R)-3-[4-(tert-butyl)-2-pyridinyl]-5-isopropyl-4,5-dihydro-5-isoxazolyl}carbonyl)amino]-5-fluoro-4-oxopentanoic acid (Iaa9);
(36) 3-({[5-ethyl-3-(4-isobutyl-2-pyridinyl)-4,5-dihydro-5-isoxazolyl]carbonyl}amino)-5-fluoro-4-oxopentanoic acid (Iaa10);
(37) 3-({[3-(4-acetyl-2-pyridinyl)-5-ethyl-4,5-dihydro-5-isoxazolyl]carbonyl}amino)-5-fluoro-4-oxopentanoic acid (Iaa11);
(38) 3-({[3-(4-cyclopropyl-2-pyridinyl)-5-ethyl-4,5-dihydro-5-isoxazolyl]carbonyl}amino)-5-fluoro-4-oxopentanoic acid (Iaa12);
(39) 3-({[3-(4-cyclopentyl-2-pyridinyl)-5-ethyl-4,5-dihydro-5-isoxazolyl]carbonyl}amino)-5-fluoro-4-oxopentanoic acid (Iaa13);
(40) 3-({[(5R)-3-(4-cyclopentyl-2-pyridinyl)-5-isopropyl-4,5-dihydro-5-isoxazolyl]carbonyl}amino)-5-fluoro-4-oxopentanoic acid (Iaa14);
(41) 3-({[3-(4-cyclohexyl-2-pyridinyl)-5-ethyl-4,5-dihydro-5-isoxazolyl]carbonyl}amino)-5-fluoro-4-oxopentanoic acid (Iaa15);
(42) 3-({[5-ethyl-3-(5,6,7,8-tetrahydro-1-isoquinolinyl)-4,5-dihydro-5-isoxazolyl]carbonyl}amino)-5-fluoro-4-oxopentanoic acid (Iaa16);
(43) 5-fluoro-3-({[5-isopropyl-3-(4-phenyl-2-pyridinyl)-4,5-dihydro-5-isoxazolyl]carbonyl}amino)-4-oxopentanoic acid (Iaa17);
(44) (3S)-5-[(diphenylphosphoryl)oxy]-3-({[(5R)-5-isopropyl-3-(1-isoquinolinyl)-4,5-dihydro-5-isoxazolyl]carbonyl}amino)-4-oxopentanoic acid (Iaa18);
(45) (3S)-3-({[(5R)-5-isopropyl-3-(1-isoquinolinyl)-4,5-dihydro-5-isoxazolyl]carbonyl}amino)-4-oxo-5-{[1-phenyl-3-(trifluoromethyl)-1H-pyrazol-5-yl]oxy}pentanoic acid (Iaa19);
(46) (3S)-5-[(4-benzyl-5-oxo-2,5-dihydro-3-furanyl)oxy-3-({[(5R)-5-isopropyl-3-(1-isoquinolinyl)-4,5-dihydro-5-isoxazolyl]carbonyl}amino)-4-oxopentanoic acid (Iaa20);
(47) (3S)-5-(isobutyryloxy)-3-({[(5R)-5-isopropyl-3-(1-isoquinolinyl)-4,5-dihydro-5-isoxazolyl]carbonyl}amino)-4-oxopentanoic acid (Iaa21);
(48) (3S)-3-({[(5R)-5-isopropyl-3-(1-isoquinolinyl)-4,5-dihydro-5-isoxazolyl]carbonyl}amino)-4-oxo-5-hexanoic acid (Iaa22);
(49) (3S)-3-({[(5R)-5-isopropyl-3-(1-isoquinolinyl)-4,5-dihydro-5-isoxazolyl]carbonyl}amino)-4-oxo-5-(2-pyridinyloxy)pentanoic acid (Iaa23);
(50) (3S)-3-({[5-ethyl-3-(2-isopropylphenyl)-4,5-dihydro-5-isoxazolyl]carbonyl}amino)-4-oxo-5-(2-pyridinyloxy)pentanoic acid (Iaa24);
(51) 2-{[(3S)-4-carboxy-3-({[(5R)-5-isopropyl-3-(1-isoquinolinyl)-4,5-dihydro-5-isoxazolyl]carbonyl}amino)-2-oxobutyl]oxy}-1-methylpyridinium trifluoromethanesulfonate (Iaa25);
(52) 2-{[(3S)-4-carboxy-3-({[5-ethyl-3-(2-isopropylphenyl)-4,5-dihydro-5-isoxazolyl]carbonyl}amino)-2-oxobutyl]oxy}-1-methylpyridinium trifluoromethanesulfonate (Iaa26);
(53) 3-({[3-(5-chloro-1-methyl-1H-indol-2-yl)-5-isopropyl-4,5-dihydro-5-isoxazolyl]carbonyl}amino)-5-fluoro-4-oxopentanoic acid (Iaa27);
(54) 3-({[3-(1,5-dimethyl-1H-indol-2-yl)-5-isopropyl-4,5-dihydro-5-isoxazolyl]carbonyl}amino)-5-fluoro-4-oxopentanoic acid (Iaa28); and
(55) (3S)-5-fluoro-3-({[(5R)-5-isopropyl-3-(1-isoquinolinyl)-4,5-dihydro-5-isoxazolyl]carbonyl}amino)-4-oxopentanoic acid (Iii-1).

The compound of formula (1) according to the present invention has two (2) asymmetric carbon atoms, and so may exist in its stereoisomeric form including diastereomer. Particularly preferred compounds among the stereoisomers are those having the following formula (1a):

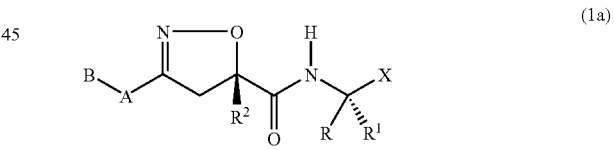

(1a)

and so it is another object of the present invention to provide the compound of formula (1a) in the stereoisomeric form.

Among the compound of formula (1a), for example, the compound of (3S)-5-fluoro-3-({[(5R)-5-isopropyl-3-(1-isoquinolinyl)-4,5-dihydro-5-isoxazolyl]carbonyl}amino)-4-oxopentanoic acid (Iii-1) may be obtained by a process comprising the steps of dissolving a mixture of (3S) and (3R) in methyl t-butyl ether, adding a small amount of crystalline (3S)-5-fluoro-3-({[(5R)-5-isopropyl-3-(1-isoquinolinyl)-4,5-dihydro-5-isoxazolyl]carbonyl}amino)-4-oxopentanoic acid as a seed material to give a crystal, and recrystallizing this crystal from ethyl acetate/n-hexane solvent system.

The most preferred compounds among the compounds of formulae (1) and (1a) are 5-fluoro-3-({[(5R)-5-isopropyl-3-(1-isoquinolinyl)-4,5-dihydro-5-isoxazolyl]carbonyl}amino)-4-oxopentanoic acid (Iii); and (3S)-5- fluoro-3-({[(5R)-5-isopropyl-3-(1-isoquinolinyl)-4,5-dihydro-5-isoxazolyl]carbonyl}amino)-4-oxopentanoic acid (Iii-1).

The processes for the preparation of the novel isoxazoline derivative of formula (1) showing an inhibitory activity against caspases are depicted in the following Reaction Schemes 1 to 5. However, those illustrated in the following Reaction Schemes represent only the typical processes used in the present invention. The manipulation order may be changed with no limit, and so the processes are not restricted to those explained below.

Reaction Scheme 1

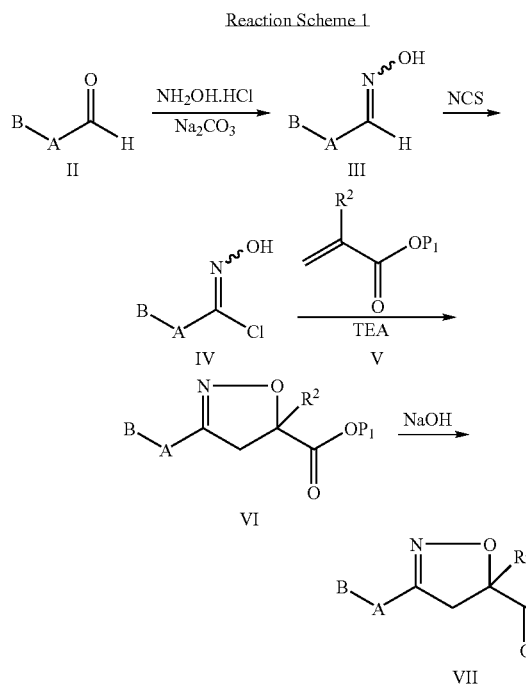

in which
A, B, and $R^2$ are defined as described above, and
$P^1$ represents simple alkyl chain.

In Reaction Scheme 1 above, an aldehyde derivative (II) is reacted with hydroxylamine-hydrochloride and sodium carbonate in a solvent mixture of alcohol-water to give an oxime derivative (III) (a mixture of syn and anti oximes). The resulting oxime derivative (III) is treated by NCS(N-chlorosuccinimide) in dimethylformamide solution to give a hydroxamoyl chloride derivative (IV). Thus obtained hydroxamoyl chloride derivative (IV) is reacted with an acrylate derivative (V) to give an isoxazoline derivative (VI), which is then hydrolyzed, if needed, to give a deprotected isoxazoline derivative (VII). If appropriate, the oxime derivative (III), the acrylate derivative (V), and NaOCl may react together in a reaction vessel (in situ) to directly give the isoxazoline derivative (VI) (see Preparations 16 and 17).

Reaction Scheme 2

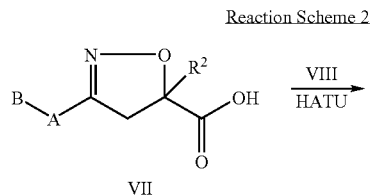

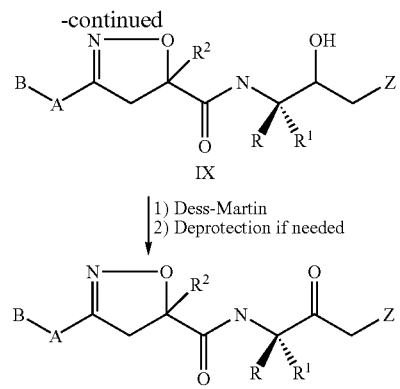

in which A, B, R, $R^1$, $R^2$, $R^{11}$, $R^{12}$, and W are defined as described above.

In Reaction Scheme 2 above, a carboxylic acid derivative (VII) is coupled with an aspartic acid derivative (VIII) (see the following Reaction Scheme 3) to give a compound (IX), which is then subjected to Dess-Martin periodinane oxidation reaction, and deprotection reaction, if needed, to give the desired compound of formula (1).

The functional group Z in the compound (1) of Reaction Scheme 2 may be formed through several steps as exemplified in the following Preparations 5 and 7 after the carboxylic acid compound (VII) on the left side is combined with an aspartic acid (β-t-Bu) methylester. Otherwise, as depicted in the following Reaction Scheme 3, the compound (VIII) already having the desired Z is synthesized first and coupled with the compound (VII) (Ref.: WO 00/23421). Further, when W is F, the racemic compound may be prepared according to a method known in *Tetrahedron Letters*, 1994, 35(52), 9693-9696.

Reaction Scheme 3

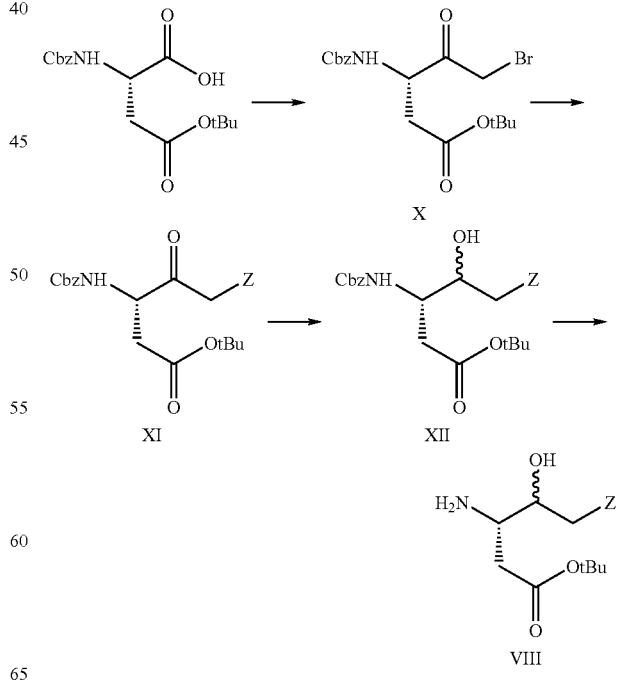

in which Z is defined as described above.

The acrylate derivative (V) used as a reactant in the above Reaction Scheme 1 may be prepared via two (2) pathways. That is, a compound (XV) can be easily prepared from a known compound (XIV) (*Synthesis*, 1982, p 924) as depicted in the following Reaction Scheme 4, or methyl (ethyl)2-i-propylacrylate, the compound (V), can be prepared from dimethyl(diethyl)malonate (*J. Chemical Society Perkin Trans.* 1 1997, 1559-1570).

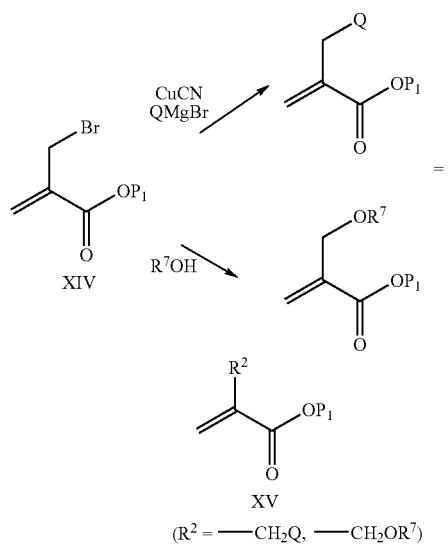

Reaction Scheme 4

($R^2 = $ —$CH_2Q$, —$CH_2OR^7$)

in which $P_1$ and $R^2$ are defined as described above.

The following Reaction Scheme 5 shows a synthetic process for preparing a compound wherein α,β-unsaturated ester or α,β-unsaturated sulfon is introduced into the $P_1$ site. According to this, the carboxylic acid derivative (VII) as prepared in Reaction Scheme 1 is reacted with an amino alcohol derivative (XVII) to give a compound (XVI), which is then subjected to Dess-Martin oxidation and Wittig reactions to give the compound (I).

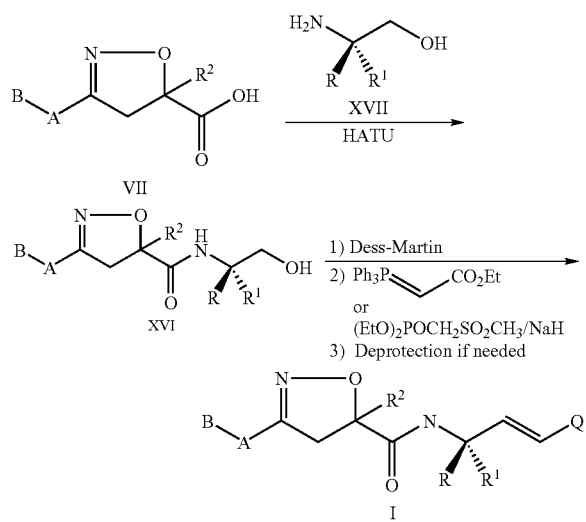

Reaction Scheme 5 in which

R, A, B, $R^1$, and $R^2$ are defined as described above, and

Q represents —$CO_2R^{13}$ or $SO_2R^{14}$, wherein $R^{13}$ and $R^{14}$ are defined as described above.

The compound of formula (1) according to the present invention has a broad spectrum of inhibitory activity against caspases as demonstrated by the results of the following Experiments, and so has an effect for preventing inflammation and apoptosis. Thus, the present invention provides a composition for inhibiting caspases, specifically a therapeutic composition for preventing inflammation and apoptosis, comprising the compound of formula (1) as an active ingredient together with the pharmaceutically acceptable carrier. Specifically, the composition of the present invention has a therapeutic effect for dementia, cerebral stroke, brain impairment due to AIDS, diabetes, gastric ulcer, cerebral injure by hepatitis, hepatitis-induced hepatic diseases, acute hepatitis, fulminant hepatic failure, liver cirrhosis, sepsis, organ transplantation rejection, rheumatic arthritis, or cardiac cell apoptosis due to ischemic cardiac diseases, particularly specifically for acute hepatitis, liver cirrhosis, or rheumatic arthritis.

Caspase inhibitor, particularly the compound of formula (1), may be formulated into various pharmaceutical forms for administration purpose. To prepare the pharmaceutical composition according to the present invention, an effective amount of the caspase inhibitor, particularly the compound of formula (1) or its salt, is mixed with a pharmaceutically acceptable carrier that may take a wide variety of forms depending on the formulation to be prepared.

The caspase inhibitor compound may be formulated as a parenteral injection, or percutaneous or oral preparation depending on its application purpose. It is especially advantageous to formulate the composition in a unit dosage form for ease of administration and uniformity of dosage.

For the oral preparation, any usual pharmaceutical carrier may be used. For example, water, glycols, oils, alcohols and the like may be used for such oral liquid preparations as suspensions, syrups, elixirs and solutions; or starches, sugars, kaolin, lubricants, binders, disintegrating agents and the like may be used for such solid preparations as powders, pills, capsules and tablets. Due to their ease of administration, tablets and capsules are the most advantageous dosage unit forms. It is also desirable for tablets and pills to be formulated into enteric-coated preparation.

For the parenteral preparation, sterile water is usually used as the carrier, though other ingredients such as solubility aids may be used. Injections, for example, sterilized aqueous or oily suspension for injection, can be prepared according to the known procedure using suitable dispersing agent, wetting agent, or suspending agent. Solvents that can be used for preparing injections include water, Ringer's fluid, and isotonic NaCl solution, and also sterilized fixing oil may be conveniently used as the solvent or suspending media. Any non-stimulative fixing oil including mono-, di-glyceride may be used for this purpose. Fatty acid such as oleic acid may also be used for injections.

For the percutaneous administration, the carrier may include a penetration enhancing agent and/or a suitable wetting agent, optionally combined with suitable additives having no significant skin irritation. Said additives may facilitate the administration through the skin and/or may assist preparation of a desired composition. These percutaneous preparations are administered via various manners, e.g., as a transdermal patch, a spot-on, or an ointment.

When the caspase inhibitor, specifically the compound of formula (1), is used for clinical purpose, it is preferably administered to the subject patient in an amount ranging from 0.1 to 100 mg per kg of body weight a day. The total daily dosage may be administered once or over several times. However, specific administration dosage for an individual patient can be varied with specific compound used, body weight, sex, hygienic condition, or diet of subject patient, time or method of administration, excretion rate, mixing ratio of agent, severity of disease to be treated, etc.

The present invention will be more specifically explained by the following examples. However, it should be understand that these examples are intended to illustrate the present invention but not in any manner to limit the scope of the present invention.

Preparation 1

Benzaldehyde Oxime

Benzaldehyde (5.31 g, 50.0 mmol) was dissolved in ethanol (60 ml)-water (30 ml), and hydroxylamine hydrochloride (5.21 g, 1.5 Eq) and anhydrous sodium carbonate ($Na_2CO_3$, 3.97 g, 0.75 Eq) were added thereto at 0° C. When a large amount of solid was formed after about one minute, water-ethanol (1:1, 60 ml) was added, and the mixture was stirred for one hour. Saturated aqueous sodium chloride solution (100 ml) was added, and the mixture was extracted twice with ethyl acetate (300 ml). The extract was washed with 1.0 N aqueous sodium bicarbonate solution ($NaHCO_3$, 100 ml×2), dried (anhydrous $Na_2SO_4$), and concentrated under reduced pressure to give the title compound (6.06 g, Yield 99%) as a white powder as a mixture of cis and trans.

$^1$H-NMR (500 MHz, $CDCl_3$) δ 8.9 (br, 1H), 8.1 (s, 1H), 7.5 (m, 2H), 7.3 (m, 3H)

Preparation 2

Benzaldehyde Hydroxamoyl Chloride

The oxime prepared in Preparation 1 (3.00 g, 24.8 mmol) was dissolved in dimethylformamide (100 ml), and N-chlorosuccinimide (3.47 g, 1.05 Eq) was added. The resulting solution was stirred for one hour in a water bath of about 40° C., and the volatile solvent was removed by distillation under reduced pressure. The residue was dissolved in ethyl acetate-hexane (1:1, 150 ml), washed with water (100 ml×3), dried (anhydrous $Na_2SO_4$), and concentrated under reduced pressure to give the title compound (3.86 g, Yield 99%). This compound was used in the next reaction without any further purification.

Preparation 3

Methyl 5-methyl-3-phenyl-4,5-dihydro-5-isoxazole-carboxylate (VIa)

The hydroxamoyl chloride prepared in Preparation 2 (3.86 g, 24.8 mmol) and methyl methacrylate (4.0 ml, 37.2 mmol, 1.5 Eq) were dissolved in dry diethylether (120 ml) under nitrogen atmosphere, the mixture was kept at −78° C., and triethylamine (6.9 ml, 2.0 Eq) was added. The mixture was stirred overnight while it was slowly warmed to room temperature. Water (100 ml) was added, and then the mixture was extracted with ethyl acetate (100 ml×2), washed with water (100 ml), dried (anhydrous $Na_2SO_4$), and concentrated under reduced pressure. The residue was purified by column chromatography (15% ethyl acetate-hexane) to give the title compound (5.34 g, Yield 98%), which was then identified by $^1$H-NMR to be 1:1 mixture of diastereomers.

$^1$H-NMR (400 MHz, $CDCl_3$) δ 6.7 (m, 2H,), 6.5 (m, 3H), 3.0 (d, J=16.7 Hz, 1H), 2.9 (s, 3H), 2.3 (d, J=16.7 Hz, 1H), 0.8 (s, 3H)

Preparation 4

5-Methyl-3-phenyl-4,5-dihydro-5-isoxazolecarboxylic Acid (VIIa)

The compound prepared in Preparation 3 (VIa, 5.34 g) was dissolved in distilled tetrahydrofuran (120 ml), and 1N aqueous sodium hydroxide solution (36.5 ml, 1.5 Eq) was added. After about four hours, the mixture was neutralized by 1N aqueous hydrochloric acid solution and distilled under reduced pressure to remove most of tetrahydrofuran. The residue was dissolved in excess ethyl acetate (>700 ml), washed with water, dried (anhydrous $Na_2SO_4$), and concentrated under reduced pressure to give the title compound (4.77 g, Yield 95%) as a white powder. This compound was used in the next reaction without any further purification.

Preparation 5

(3S)-3-{[(benzyloxy)carbonyl]amino}-5-(t-butoxy)-2-hydroxy-5-oxopentyl 2,6-dichlorobenzoate (XIIa)

To N-benzyloxycarbonyl-β-t-butylaspartic acid (5.03 g, 15.6 mmol) and NMM (1.90 ml, 17.1 mmol) was added dry tetrahydrofuran (60 ml) under nitrogen atmosphere, the mixture was kept −15□, and isobutyl chloroformate (2.12 ml, 16.3 mmol) was added thereto. The mixture was stirred for about 20 minutes. To the reaction mixture being kept at 0□ was added diazomethane-ether solution (synthesized from 2.0 Eq of 1-methyl-3-nitro-1-nitroso-guanidine, 60 ml) to prepare diazoketone derivative (~30 minutes). 30% HBr/AcOH (6.42 ml, 2.0 Eq) was added thereto at 0° C. The resulting mixture was stirred (30-60 minutes), extracted with ethyl acetate, washed twice with saturated aqueous sodium bicarbonate solution and once with aqueous sodium chloride solution, dried (anhydrous $Na_2SO_4$), and concentrated under reduced pressure to give bromomethyl ketone derivative (X, 6.4 g).

Thus obtained bromomethyl ketone derivative (X, 4.36 g) and 2,6-dichlorobenzoic acid (2.28 g, 1.1 Eq) were dissolved in dimethylformamide (18 ml), KF (1.58 g, 2.5 Eq) was added, and the mixture was stirred for two hours to give 2,6-dichlorobenzoyloxymethyl ketone derivative (XIa). This compound was dissolved in methanol (20 ml) and reacted by adding $NaBH_4$ (412 mg)-methanol solution (40 ml)(−10□~room temperature, two hours). The reaction was stopped by acetic acid, and the reaction solution was distilled under reduced pressure to remove methanol. The residue was extracted with ethyl acetate (50 ml×2), washed with water and aqueous sodium chloride solution, dried (anhydrous $Na_2SO_4$), concentrated under reduced pressure, and separated-purified by column chromatography (ethyl acetate-hexane, 1:5) to give the title compound (4.80 g, Yield 86%) in a diastereomeric form.

$^1$H-NMR (400 MHz, $CDCl_3$) δ 7.3-7.2 (m, 8H), 5.9 (m, 1H), 5.2 (m, 4H), 4.7 (m, 1H), 2.9 (m, 1H), 2.7 (m, 1H), 1.4 (s, 9H)

Preparation 6

(3S)-3-amino-5-(t-butoxy)-2-hydroxy-5-oxopentyl 2,6-dichlorobenzoate (VIIIa)

The benzyloxycarbonyl group of the compound prepared in Preparation 5 was removed (Pd/C) under hydrogen balloon for 40 minutes to give the title compound (Yield 100%).

$^1$H-NMR (400 MHz, DMSO-d$_6$) δ 8.2 (br, 2H), 7.6-7.5 (m, 3H), 6.1 (m, 1H), 4.4-3.9 (m, 3H), 3.0-2.6 (m, 2H), 1.4 (s, 9H)

Example 1

(3S)-5-(t-butoxy)-3-{[(5-methyl-3-phenyl-4,5-dihydro-5-isoxazolyl)carbonyl]amino}-2,5-dioxopentyl 2,6-dichlorobenzoate (Ia)

A mixture of the carboxylic acid derivative prepared in Preparation 4 (VIIa, 300 mg, 1.46 mmol), the amino alcohol derivative prepared in Preparation 6 (VIIIa, 667 mg, 1.1 Eq) and HATU (722 mg, 1.3 Eq) was cooled to 0☐, triethylamine (0.82 ml, 4.0 Eq) was added in a solvent of DMF (5 ml), and the resulting mixture was reacted for 5 hours. The solvent was distilled under reduced pressure, and the residue was extracted with ethyl acetate (200 ml×2), washed with water, aqueous sodium bicarbonate solution, and aqueous sodium chloride solution, dried (anhydrous Na$_2$SO$_4$), concentrated under reduced pressure, and purified by column chromatography to give Compound (IXa) (810 mg, Yield 98%). To this compound and Dess-Martin reagent (1.70 g, 3.0 Eq) was added dry dichloromethane (25 ml), and the mixture was stirred for one hour at room temperature. The reaction was stopped by isopropyl alcohol (3 ml). The solid was removed by filtration under reduced pressure through Celite, and the filtrate was extracted with ethyl acetate (20 ml×2), washed with water, saturated aqueous sodium bicarbonate solution and aqueous sodium chloride solution, dried (anhydrous Na$_2$SO$_4$), concentrated under reduced pressure, and preliminarily purified by column chromatography (36% ethyl acetate-hexane) to give the diastereomeric title compound (780 mg).

$^1$H-NMR (400 MHz, CDCl$_3$) δ 7.8 (m, NH, 1H), 7.6 (m, 2H), 7.3 (m, 3H), 7.2 (m, 3H), 5.1-5.0 (m, 2H), 4.8 (m, 1H), 3.8 (m, 1H), 3.2 (m, 1H), 2.9-2.8 (m, 2H), 1.7 (s, 3H), 1.4 (s, 9H)

Example 2

(3S)-5-[(2,6-dichlorobenzoyl)oxy]-3-{[(5-methyl-3-phenyl-4,5-dihydro-5-isoxazolyl)carbonyl]amino}-4-oxopentan-oic acid (Iaa)

The compound prepared in Example 1 (44 mg) was dissolved in dichloromethane (2 ml), and trifluoroacetic acid (1 ml) was added at 0☐. The mixture was stirred for two hours while it was slowly warmed to room temperature, and then concentrated under reduced pressure to give the title compound (Iaa) in a stoichiometric amount.

$^1$H-NMR (500 MHz, CDCl$_3$) δ 8.1 (m, 1H), 7.5 ((m, 2H), 7.3 (m, 3H), 7.2 (m, 3H), 5.1-4.9 (m, 2H), 4.9-4.8 (m, 1H), 3.8 (m, 1H), 3.2 (m, 1H), 1.7 (m, 3H)

Preparation 7 t-Butyl (3S)-3-amino-4-hydroxy-5-phenoxypentanoate (VIIIb)

To N-benzyloxycarbonyl-β-t-butyl-aspartic acid (10.0 g, 31.0 mmol) and NMM (3.75 ml, 1.1 Eq) was added dry tetrahydrofuran (120 ml) under nitrogen atmosphere, and the mixture was kept at −15☐. Isobutyl chloroformate (4.22 ml, 1.05 Eq) was added thereto, and the mixture was stirred for about 20 minutes. The reactants were kept at 0☐, which was then mixed with diazomethane-ether solution (synthesized from 2.0 Eq of 1-methyl-3-nitro-1-nitrosoguanidine, 60 ml) to prepare diazoketone derivative (~30 minutes). 30% HBr/AcOH (12.83 ml, 2.0 Eq) was added thereto to prepare bromomethyl ketone derivative (30-60 minutes). The product was extracted with ethyl acetate, washed twice with saturated aqueous sodium bicarbonate solution and aqueous sodium chloride solution, dried (anhydrous Na$_2$SO$_4$), and concentrated under reduced pressure to give bromomethyl ketone derivative (12.9 g) in a stoichiometric amount.

Thus obtained bromomethyl ketone derivative (X, 12.9 g, 31.0 mmol) and phenol (3.23 g, 1.2 Eq) were dissolved in dimethylformamide (30 ml), KF(4.53 g, 2.5 Eq) was added, and the mixture was stirred for two hours to give phenoxymethyl ketone derivative (XIb). This compound was dissolved in methanol (40 ml)-THF (100 ml) and was reacted by adding NaBH$_4$ (2.35 g)-methanol solution (40 ml) (−10☐-room temperature, two hours). The reaction was stopped by acetic acid, and the reaction mixture was distilled under reduced pressure to remove methanol. The residue was extracted with ethyl acetate (50 ml×2), washed with water and aqueous sodium chloride solution, dried (anhydrous Na$_2$SO$_4$), concentrated under reduced pressure, and separated-purified by column chromatography (ethyl acetate-hexane, 1:7) to give a compound (XIIb, 6.50 g, Yield 50%) in a diastereomeric form of which amino group is protected by benzyloxycarbonyl.

$^1$H-NMR (400 MHz, CDCl$_3$) δ 7.3-7.2 (m, 8H), 5.9 (m, 1H), 5.2 (m, 4H), 4.7 (m, 1H), 2.9 (m, 1H), 2.7 (m, 1H), 1.4 (s, 9H)

The benzyloxycarbonyl group of the compound obtained above was removed (Pd/C) under hydrogen balloon to give the title compound (4.16 g, Yield 95%).

$^1$H-NMR (400 MHz, DMSO-d$_6$) δ 8.1 (br, 2H), 7.3 (m, 5H), 5.6 (m, 1H), 4.1-4.0 (m, 3H), 2.6 (m, 2H), 1.4 (s, 9H)

Example 3 t-butyl (3S)-3-{[(5-methyl-3-phenyl-4,5-dihydro-5-isoxazolyl)carbonyl]amino}-4-oxo-5-phenoxypentanoate (Ib)

A mixture of the carboxylic acid derivative prepared in Preparation 4 (VIIa, 273 mg, 1.33 mmol), the amino alcohol derivative prepared in Preparation 7 (VIIIb, 412 mg, 1.1 Eq) and HATU (657 mg, 1.3 Eq) was cooled to 0☐, triethylamine (0.74 ml, 4.0 Eq) was added in a solvent of DMF (5 ml), and the resulting mixture was reacted for 5 hours. The solvent was distilled under reduced pressure, and the residue was extracted with ethyl acetate (200 ml×2), washed with water, aqueous sodium bicarbonate solution, and aqueous sodium chloride solution, dried (anhydrous Na$_2$SO$_4$), concentrated under reduced pressure, and purified by column chromatography (30-40% EA/Hex) to give Compound (IXb) (545 mg, Yield 88%). To this compound and Dess-Martin reagent (1.43 g, 3.0 Eq) was added dry dichloromethane (25 ml), and the mixture was stirred for one hour at room temperature. The reaction was stopped by isopropyl alcohol (2 ml). The solid was removed by filtration under reduced pressure through Celite, and the filtrate was extracted with ethyl acetate (20 ml×2), washed with water, saturated aqueous sodium bicarbonate solution and aqueous sodium chloride solution, dried (anhydrous Na$_2$SO$_4$), concentrated under reduced pressure, and preliminarily purified by column chromatography (eluent: 25% ethyl acetate-hexane) to give the diastereomeric title compound (540 mg, Yield 99%).

$^1$H-NMR (400 MHz, CDCl$_3$) δ 7.8 (NH, 1H), 7.5 (m, 2H), 7.3 (m, 3H), 7.3 (m, 1H), 7.1 (m, 1H), 6.8 (m, 2H), 6.7 (m, 1H), 4.9 (s, 1H), 4.7-4.6 (m, 2H), 3.7 (d, J=17 Hz, 1H), 3.2 (d, J=17 Hz, 1H), 2.9 (m, 1H), 2.8 (m, 1H), 1.7 (s, 3H), 1.4 (s, 9H)

Example 4

(3S)-3-{[(5-methyl-3-phenyl-4,5-dihydro-5-isoxazolyl)carbonyl]amino}-4-oxo-5-phenoxypentanoic Acid (Ibb)

The compound prepared in Example 3 (530 mg, 1.136 mmol) was dissolved in dichloromethane (6 ml), and trifluoroacetic acid (3 ml) was added at 0□. The mixture was stirred for two hours while it was slowly warmed to room temperature, and concentrated under reduced pressure to give the title compound (Ibb) (465 mg) with a stoichiometric yield.

$^1$H-NMR (400 MHz, CDCl$_3$) δ 7.5 (m, 2H), 7.3 (m, 3H), 7.1 (NH, 1H), 6.7 (m, 5H), 5.0-4.6 (m, 2H), 4.2 (m, 1H), 3.8 (m, 1H), 3.2 (m, 1H), 3.0-2.7 (m, 2H), 1.6 (s, 3H)

Preparation 8

Ethyl 2-ethylacrylate (Vb)

To CuCN (26.9 g, dried in advance under vacuum) was added under nitrogen atmosphere about 500 ml of dry tetrahydrofuran. The mixture was kept at −78□, and 100 ml of methyl magnesium bromide (3.0M diethylether solution) was slowly added thereto under mechanical stirring. The thick mixture was stirred for about 30 minutes at −78□. Ethyl 2-bromomethylacrylate (28.9 g, 150 mmol, Synthetic method: Villieras, J. and Rambaud, M. Synthesis, 1982, 914) dissolved in about 30 ml of dry tetrahydrofuran was slowly added thereto. The temperature of the reaction mixture was slowly raised to room temperature over two hours. The reaction was completed by slowly adding saturated ammonium chloride solution (~50 ml). The reaction mixture was filtered through Celite to remove the precipitates, and then washed with diethylether. The organic layer was washed with water and saturated sodium bicarbonate solution (300 ml×2), dried (anhydrous Na$_2$SO$_4$), and concentrated under reduced pressure to give 26.7 g (stoichiometric yield) of a transparent liquid. This liquid was identified by $^1$H-NMR (500 MHz, CDCl$_3$) and was confirmed to be the title compound having about 75% of w/w purity.

$^1$H-NMR (500 MHz, CDCl$_3$) δ 6.12 (1H, s), 5.50 (1H, s), 4.20 (2H, q, J=7.3 Hz), 2.31 (2H, qt), 1.28 (3H, t, J=7.3 Hz), 1.07 (3H, t, J=7.8 Hz)

Preparation 9

Ethyl 5-ethyl-3-phenyl-4,5-dihydro-5-isoxazolecarboxylate (VIb)

The compound of Preparation 8 (XVa) was reacted according to the same procedure as Preparation 3 to give the title compound.

$^1$H-NMR (400 MHz, CDCl$_3$) δ 7.6 (m, 2H), 7.4-7.3 (m, 3H), 4.3-4.2 (m, 2H), 4.0 (d, J=17.2 Hz, 1H), 3.4 (d, J=17.2 Hz, 1H), 2.1-2.0 (m, 2H), 1.3 (t, 3H), 1.0 (t, 3H)

Preparation 10 t-Butyl (3S)-3-amino-4-hydroxy-5-(2,3,5,6-tetrafluorophenoxy) pentanoate (VIIIc)

2,3,5,6-Tetrafluorophenol was reacted according to the same procedure as Preparations 5 and 6 to give the title compound in a total yield of 72%.

$^1$H-NMR (400 MHz, DMSO-d$_6$) δ 8.2 (br, 2H), 7.6-7.5 (m, 1H), 5.9 (m, 1H), 4.3-4.1 (m, 3H), 3.6 (m, 1H), 2.7 (m, 1H), 1.4 (s, 9H)

Example 5 t-Butyl (3S)-3-{[(5-ethyl-3-phenyl-4,5-dihydro-5-isoxazolyl)carbonyl]amino}-4-oxo-5-(2,3,5,6-tetrafluorophenoxy)pentanoate (Ic)

The compounds of Preparations 9 and 10 were reacted according to the same procedure as Preparation 4 and Example 1 to give the title compound.

$^1$H-NMR (400 MHz, CDCl$_3$) δ 7.6 (dd, J=3.6, 1.6 Hz, 1H), 7.6 (m, 2H), 7.4-7.3 (m, 3H), 6.7 (m, 1H), 5.1-4.9 (m, 2H), 4.9-4.8 (m, 1H), 3.7 (dd, J=17.6, 17.2 Hz, 1H), 3.3 (1H, d, J=17.2 Hz), 3.0-2.8 (m, 1H), 2.8-2.7 (m, 1H), 2.1 (m, 1H), 1.9 (m, 1H), 1.4-1.3 (two s, 9H,), 1.0 (m, 3H)

Example 6

(3S)-3-{[(5-ethyl-3-phenyl-4,5-dihydro-5-isoxazolyl)carbonyl]amino}-4-oxo-5-(2,3,5,6-tetrafluorophenoxy)pentanoic acid (Icc)

The compound of Example 5 was reacted according to the same procedure as Example 2 to give the title compound.

$^1$H-NMR (400 MHz, DMSO-d$_6$) δ 7.6 (br, 1H), 7.6-7.5 (m, 2H), 7.4-7.3 (m, 3H), 6.8-6.7 (m, 1H), 4.9-4.8 (m, 1H), 4.5 (br, 2H), 3.7 (d, J=16 Hz, 1H), 3.3 (d, J=16 Hz, 1H), 3.3-3.0 (m, 1H), 2.8-2.7 (m, 1H), 2.1 (m, 1H), 2.0-1.9 (m, 1H), 1.0 (m, 3H)

MS [M+H]$^+$ 497

Preparation 11

Ethyl 5-ethyl-3-(1-naphthyl)-4,5-dihydro-5-isoxazolecarboxylate (VIc)

1-Naphthaldehyde and ethyl 2-ethylacrylate were reacted according to the same procedure as Preparations 1, 2, and 3 to give the title compound.

$^1$H-NMR (400 MHz, CDCl$_3$) δ 8.9 (d, J=8.8 Hz, 1H), 7.9-7.8 (m, 2H), 7.6-7.4 (m, 4H), 4.3-4.2 (m, 2H), 4.0 (d, J=17.2 Hz, 1H), 3.4 (d, J=17.2 Hz, 1H), 2.1-2.0 (m, 2H), 1.3 (t, 3H), 1.0 (t, 3H)

Example 7 t-Butyl (3S)-3-({[5-ethyl-3-(1-naphthyl)-4,5-dihydro-5-isoxazolyl]carbonyl}amino)-4-oxo-5-(2,3,5,6-tetrafluorophenoxy)pentanoate (Id)

The compounds of Preparations 11 and 10 were reacted according to the same procedure as Preparation 4 and Example 1 to give the title compound.

$^1$H-NMR (400 MHz, CDCl$_3$) δ 8.9 (m, 1H), 7.9-7.8 (m, 3H), 7.6-7.4 (m, 4H), 6.5-6.9 (m, 1H), 5.1-4.9 (m, 2H), 4.9 (m, 1H), 3.9 (dd, 1H), 3.5 (d, J=17.2 Hz, 1H), 3.0-2.9 (m, 1H), 2.8 (m, 1H), 2.2 (m, 1H), 2.0 (m, 1H), 1.4-1.3 (two s, 9H), 1.1 (m, 3H)

Example 8

(3S)-3-({[5-ethyl-3-(1-naphthyl)-4,5-dihydro-5-isoxazolyl]carbonyl}amino)-4-oxo-5-(2,3,5,6-tetrafluorophenoxy)pentanoic Acid (Idd)

The compound of Example 7 was reacted according to the same procedure as Example 2 to give the title compound.

¹H-NMR (400 MHz, CDCl₃) δ 8.8 (m, 1H), 7.9-7.7 (m, 3H), 7.6-7.4 (m, 4H), 6.7 (m, 1H), 4.9 (m, 1H), 4.5 (br, 2H), 3.9 (d, J=17.2 Hz, 1H), 3.5 (d, J=17.2 Hz, 1H), 3.1-2.9 (m, 1H), 2.8-2.7 (m, 1H), 2.2 (m, 1H), 2.0 (m, 1H), 1.0 (m, 3H)
MS [M+MeOH+Na]+601

Preparation 12

Ethyl 5-ethyl-3-(2-naphthyl)-4,5-dihydro-5-isoxazolecarboxylate (VId)

2-Naphthaldehyde and ethyl 2-ethylacrylate were reacted according to the same procedure as Preparations 1, 2, and 3 to give the title compound.
¹H-NMR (500 MHz, CDCl₃) δ 8.7 (d, J=8.8 Hz, 1H), 7.8-7.7 (m, 2H), 7.5-7.3 (m, 4H), 4.3-4.2 (m, 2H), 4.0 (d, J=17.2 Hz, 1H), 3.4 (d, J=17.2 Hz, 1H), 2.1-2.0 (m, 2H), 1.3 (t, 3H), 1.0 (t, 3H)

Example 9 t-Butyl (3S)-3-({[5-ethyl-3-(2-naphthyl)-4,5-dihydro-5-isoxazolyl]carbonyl}amino)-4-oxo-5-(2,3,5,6-tetrafluorophenoxy)pentanoate (Ie)

The compounds of Preparations 12 and 10 were reacted according to the same procedure as Preparation 4 and Example 1 to give the title compound.
¹H-NMR (400 MHz, CDCl₃) δ 7.8-7.7 (m, 6H), 7.5 (m, 2H), 6.7 & 6.5 (m, 1H), 5.1-4.9 (m, 2H), 4.9-4.8 (m, 2H), 3.8 (dd, J=16 Hz, 1H), 3.4 (d, J=16 Hz, 1H), 3.0 (m, 1H), 2.8 (m, 1H), 2.8-2.7 (m, 1H), 2.2-2.1 (m, 1H), 2.0 (m, 1H), 1.4-1.3 (two s, 9H), 1.1-1.0 (m, 3H)

Example 10

(3S)-3-({[5-ethyl-3-(2-naphthyl)-4,5-dihydro-5-isoxazolyl]carbonyl}amino)-4-oxo-5-(2,3,5,6-tetra fluorophenoxy)pentanoic acid (Iee)

The compound of Example 9 was deprotected according to the same procedure as Example 2, and the isomers were resolved by prep-TLC to give the following two compounds.
Weakly Polar Diastereomer:
¹H-NMR (400 MHz, DMSO-d₆) δ 12.4 (br, 1H), 8.7 (br, 1H), 8.1 (s, 1H), 7.9-8.0 (m, 3H), 7.8-7.9 (m, 1H), 7.5-7.6 (m, 3H), 5.2 (br, 2H), 4.7 (br, 1H), 3.8 (d, J=17.2 Hz, 1H), 3.5 (d, J=17.6 Hz, 1H), 2.7 (m, 1H), 2.5 (m, 1H), 2.0 (m, 1H), 1.9 (m, 1H), 0.9-0.8 (m, 3H)
MS [M+H]⁺ 547
Highly Polar Diastereomer:
¹H-NMR (400 MHz, DMSO-d₆) δ 8.6 (br, 1H), 8.2 (s, 1H), 8.0-7.9 (m, 3H), 7.9 (m, 1H), 7.6 (m, 2H), 7.4 (m, 1H), 5.0 (br, 2H), 4.8 (m, 1H), 3.9 (d, J=17.6 Hz, 1H,), 3.6 (d, J=17.6 Hz, 1H,), 2.9-2.7 (m, 2H), 2.1-2.0 (m, 2H), 2.0-1.9 (m, 1H), 0.9 (m, 3H)

Preparation 13

Ethyl 5-ethyl-3-(1-isoquinolinyl)-4,5-dihydro-5-isoxazolecarboxylate (VIe)

1-Isoquinolinealdehyde and ethyl 2-ethylacrylate were reacted according to the same procedure as Preparations 1, 2 and 3. The title compound in an active chiral isomeric form was separated by Chiral OD HPLC (Daicel Chemical Industries, 2.00 cm×25 cm, OD00CJ-IC005, 3% i-PrOH in Hexane, 220 nm), which was then used in the next reaction.
¹H-NMR (400 MHz, CDCl₃) δ 9.25 (m, 1H), 8.55 (d, 1H), 7.85 (d, 1H), 7.74-7.65 (m, 3H), 4.29 (m, 2H), 4.13 (d, 1H), 3.71 (d, 1H), 2.11 (m, 2H), 1.33 (t, 3H), 1.06 (t, 3H)

Example 11 t-Butyl (3S)-3-({[5-ethyl-3-(1-isoquinolinyl)-4,5-dihydro-5-isoxazolyl]carbonyl}amino)-4-oxo-5-(2,3,5,6-tetrafluorophenoxy)pentanoate (If)

The compounds of Preparations 13 and 10 were reacted according to the same procedure as Preparation 4 and Example 1 to give the title compound.
¹H-NMR (400 MHz, CDCl₃) δ 9.14 (m, 1H), 8.53 (m, 1H), 7.91-7.85 (m, 2H), 7.74-7.64 (m, 3H), 6.73-6.62 (m, 1H), 5.30-4.91 (m, 3H), 4.09 (two d, 1H), 3.72 (two d, 1H), 3.04-2.76 (m, 2H), 2.24 (m, 1H), 2.04 (m, 1H), 1.45 & 1.35 (two s, 9H), 1.08 (two t, 3H)

Example 12

(3S)-3-({[5-ethyl-3-(1-isoquinolinyl)-4,5-dihydro-5-isoxazolyl]carbonyl}amino)-4-oxo-5-(2,3,5,6-tetrafluorophenoxy)pentanoic acid (Iff)

The compound of Example 11 was reacted according to the same procedure as Example 2 to give the title compound.
¹H-NMR (400 MHz, DMSO-d₆) δ 9.02 (m, 1H), 8.76 (m, 1H), 8.59 (m, 1H), 8.08-7.73 (m, 4H), 7.61-7.32 (m, 1H), 5.19-5.10 (m, 2H), 4.93-4.65 (m, 1H), 3.91 (two d, 1H), 3.68 (two d, 1H), 2.91-2.52 (m, 2H), 2.10-1.94 (m, 2H), 0.94 (two t, 3H)
Mass: M+H 548

Example 13 t-Butyl 3-({[5-ethyl-3-(1-isoquinolinyl)-4,5-dihydro-5-isoxazolyl]carbonyl}amino)-5-fluoro-4-oxopentanoate (Ig)

The compound of Preparation 13 and t-butyl 3-amino-5-fluoro-4-hydroxypentanoate were reacted according to the same procedure as Preparation 4 and Example 1 to give the title compound.
¹H-NMR (400 MHz, CDCl₃) δ 9.15 (m, 1H), 8.55 (d, 1H), 7.87-7.66 (m, 5H), 5.22-4.89 (m, 3H), 4.12 (two d, 1H), 3.72 (two d, 1H), 3.05-2.75 (m, 2H), 2.22 (m, 1H), 2.04 (m, 1H), 1.45 & 1.34 (two s, 9H), 1.07 (two t, 3H)

Example 14

3-({[5-Ethyl-3-(1-isoquinolinyl)-4,5-dihydro-5-isoxazolyl]carbonyl}amino)-5-fluoro-4-oxopentanoic acid (Igg)

The compound of Example 13 was reacted according to the same procedure as Example 2 to give the title compound.
¹H-NMR (400 MHz, DMSO-d₆) δ 9.03 (m, 1H), 8.67-8.59 (m, 2H), 8.08 (d, 1H), 7.97-7.78 (m, 3H), 5.26-5.07 (m, 2H), 4.75 (m, 1H), 3.94 (two d, 1H), 3.67 (two d, 1H), 2.88-2.58 (m, 2H), 2.07-1.94 (m, 2H), 0.96 (two t, 3H)
Mass: M+H 402

Example 15

Ethyl 3-({[5-ethyl-3-(1-isoquinolinyl)-4,5-dihydro-5-isoxazolyl]carbonyl}amino)-5-fluoro-4-oxopentanoate (Ihh)

The compound of Example 14 was reacted according to a method known in *Tetrahedron Letters,* 1994, 35(52), 9693-9696 to give the title compound.
¹H-NMR (400 MHz, CDCl₃) δ 9.15 (m, 1H), 8.55 (d, 1H), 7.89-7.67 (m, 5H), 5.23-4.94 (m, 3H), 4.18 (m, 2H), 4.11 (two d, 1H), 3.72 (two d, 1H), 3.08-2.82 (m, 2H), 2.22 (m, 1H), 2.05 (m, 1H), 1.29-1.04 (m, 6H)

Preparation 14

Methyl 5-isopropyl-3-(1-isoquinolinyl)-4,5-dihydro-5-isoxazolecarboxylate) and Resolution (VIf)

1-Isoquinolinealdehyde and methyl 2-isopropylacrylate were reacted according to the same procedure as Preparations 1, 2 and 3 to give the title compound. From thus obtained compound, (5R)-active chiral isomer (9.7 min-11.7 min) was separated by prep-HPLC using chiral OD column (Daicel Chemical Industries, 2.00 cm×25 cm, OD00CJ-1C005, 5% i-PrOH in Hexane, 14 ml/min, 220 nm) (the other (5S)-isomer was eluted during the retention time of 15.3-20.1 min), which was then used in the next reaction (see Preparation 23 for the resolution after hydrolysis)

$^1$H-NMR (500 MHz, CDCl$_3$) δ 9.24 (m, 1H), 8.55 (d, 1H), 7.85 (d, 1H), 7.72 (t, 3H), 7.67 (m, 2H), 4.11 (d, 1H), 3.83 (s, 3H), 3.74 (d, 1H), 2.50 (septet, 1H), 1.07 (d, 3H), 1.02 (d, 3H)

Example 16 t-Butyl 5-fluoro-3-({[(5R)-5-isopropyl-3-(1-isoquinolinyl)-4,5-dihydro-5-isoxazolyl]carbonyl}amino)-4-oxopentanoate (Ih)

The compound of Preparation 14 and t-butyl 3-amino-5-fluoro-4-hydroxypentanoate were reacted according to the same procedure as Preparation 4 and Example 1 to give the title compound.

$^1$H-NMR (500 MHz, CDCl$_3$) δ 9.14 (m, 1H), 8.55 (d, 1H), 7.87-7.65 (m, 5H), 5.23-4.93 (m, 2H), 4.90 (m, 1H), 4.05-4.00 (two d, 1H), 3.84-3.79 (two, 1H), 3.06-2.74 (m, 2H), 2.40 (m, 1H), 1.45 & 1.34 (two s, 9H), 1.12-1.07 (m, 6H)

Example 17

5-Fluoro-3-({[(5R)-5-isopropyl-3-(1-isoquinolinyl)-4,5-dihydro-5-isoxazolyl]carbonyl}amino)-4-oxopentanoic acid (Iii)

The compound of Example 16 was reacted according to the same procedure as Example 2 to give the title compound (the compound of (5S)-isomer, Iii-u, was obtained according to the same procedure).

$^1$H-NMR (400 MHz, DMSO-d$_6$) δ 9.00 (m, 1H), 8.63-8.48 (m, 2H), 8.08 (d, 1H), 7.97 (m, 1H) 7.87-7.76 (m, 2H), 5.31-4.82 (br, 2H), 4.74 (m, 1H), 3.91 (two d, 1H), 3.73 (two d, 1H), 2.88-2.61 (m, 2H), 2.33 (m, 1H), 0.98 (m, 6H)
Mass: M+H 416

Preparation 15

Ethyl 5-ethyl-3-(4-quinolinyl)-4,5-dihydro-5-isoxazolecarboxylate (VIg)

4-Quinolinealdehyde and ethyl 2-ethylacrylate were reacted according to the same procedure as Preparations 1, 2, and 3 to give the title compound.

$^1$H-NMR (400 MHz, CDCl$_3$) δ 8.95 (d, 1H), 8.89 (m, 1H), 8.11 (d, 1H), 7.83 (m, 1H), 7.71 (m, 1H), 7.65 (d, 1H), 4.27 (m, 2H), 4.01 (d, 1H), 3.67 (d, 1H), 2.10 (m, 2H), 1.31 (t, 3H), 1.02 (t, 3H)

Example 18 t-Butyl 3-({[5-ethyl-3-(4-quinolinyl)-4,5-dihydro-5-isoxazolyl]carbonyl}amino)-5-fluoro-4-oxopentanoate (Ii)

The compound of Preparation 15 and t-butyl 3-amino-5-fluoro-4-hydroxypentanoate were reacted according to the same procedure as Preparation 4 and Example 1 to give the title compound.

$^1$H-NMR (400 MHz, CDCl$_3$) δ 8.97 (d, 1H), 8.89 (m, 1H), 8.17 (d, 1H), 7.87-7.64 (m, 3H), 7.36 (d, 1H), 5.21-4.93 (m, 3H), 3.93 (two d, 1H), 3.48 (two d, 1H), 3.05-2.78 (m, 2H), 2.24 (m, 1H), 2.03 (m, 1H), 1.46 & 1.33 (two s, 9H), 1.06 (two t, 3H)

Example 19

3-({[5-Ethyl-3-(4-quinolinyl)-4,5-dihydro-5-isoxazolyl]carbonyl}amino)-5-fluoro-4-oxopentanoic acid (Ijj)

The compound of Example 18 was reacted according to the same procedure as Example 2 to give the title compound.

$^1$H-NMR (400 MHz, DMSO-d$_6$) δ 9.16-9.10 (m, 2H), 8.25-7.86 (m, 5H), 5.20 (br, 2H), 4.75 (m, 1H), 4.00-3.89 (two d, 1H), 3.73 (two d, 1H), 2.87-2.71 (m, 2H), 2.26-2.05 (m, 2H), 1.07 (two t, 3H)
Mass: M+H 402

Preparation 16

Ethyl 3-(benzothiophen-2-yl)-5-ethyl-4,5-dihydro-5-isoxazolecarboxylate (VIh)

Benzothiophen-2-aldehyde oxime derivative (400 mg, 2.26 mmol) prepared according to the same procedure as Preparation 1 was dissolved in THF (25 ml), and the mixture was kept at 0□. Ethyl 2-ethylacrylate (434 mg, 1.5 Eq) and triethylamine (7 drops) were dissolved in THF (5 ml), thus obtained solution was slowly added to the above, and sodium hypochlorite solution (6.0 ml) was further added. The reaction solution was warmed to room temperature and stirred for 4 hours. Water (20 ml) was added, and the mixture was extracted with ethyl acetate (40 ml×2), washed with aqueous sodium chloride solution (20 ml), dried over magnesium sulfate, filtered, and concentrated under reduced pressure. The residue was purified by column chromatography (20% ethyl acetate-hexane) to give the title compound (121 mg, Yield 18%).

$^1$H-NMR (400 MHz, CDCl$_3$) δ 7.82-7.75 (m, 2H), 7.40-7.32 (m, 3H), 4.28 (m, 2H), 3.90 (d, 1H), 3.31 (d, 1H), 2.07 (m, 2H), 1.33 (t, 3H), 1.01 (t, 3H)

Example 20 t-Butyl 3-({[3-(benzothiophene-2-yl)-5-ethyl-4,5-dihydro-5-isoxazolyl]carbonyl}amino)-5-fluoro-4-oxopentanoate (Ij)

The compound of Preparation 16 and t-butyl 3-amino-5-fluoro-4-hydroxypentanoate were reacted according to the same procedure as Preparation 4 and Example 1 to give the title compound.

$^1$H-NMR (400 MHz, CDCl$_3$) δ 7.83-7.68 (m, 3H), 7.42-7.35 (m, 3H), 5.21-4.88 (m, 3H), 3.80 (two d, 1H), 3.38 (two d, 1H), 3.03-2.78 (m, 2H), 2.17 (m, 1H), 2.01 (m, 1H), 1.46 & 1.38 (two s, 9H), 1.03 (two t, 3H)

Example 21

3-({[3-(benzothiophen-2-yl)-5-ethyl-4,5-dihydro-5-isoxazolyl]carbonyl}amino)-5-fluoro-4-oxopentanoic acid (3-({[3-(benzothiophen-2-yl)-5-ethyl-4,5-dihydro-5-isoxazolyl]carbonyl}amino)-5-fluoro-4-oxopentanoic Acid) (Ikk)

The compound of Example 20 was reacted according to the same procedure as Example 2 to give the title compound.
$^1$H-NMR (400 MHz, DMSO-d$_6$) δ 8.63 (m, 1H), 8.11-7.79 (m, 3H), 7.47-7.36 (m, 2H), 5.24-5.06 (m, 2H), 4.73 (m, 1H), 3.79 (two d, 1H), 3.53 (two d, 1H), 2.83-2.58 (m, 2H), 2.03-1.86 (m, 2H), 0.91 (two t, 3H)
Mass: M+H 407

Preparation 17

Ethyl 3-(1,3-dimethyl-1H-indol-2-yl)-5-ethyl-4,5-dihydro-5-isoxazolecarboxylate (VIi)

1,3-Dimethyl-1H-indol-2-aldehyde oxime derivative (356 mg, 2.07 mmol) was dissolved in dichloromethane (20 ml), and the mixture was kept at 0□. Ethyl 2-ethylacrylate (345 mg, 1.3 Eq) and triethylamine (6 drops) were dissolved in dichloromethane (5 ml), thus obtained solution was slowly added to the above, and sodium hypochlorite solution (5.5 ml) was further added. The reaction solution was warmed to room temperature and stirred for 4 hours. Water (20 ml) was added, and the mixture was extracted with dichloromethane (40 ml×2), washed with aqueous sodium chloride solution (20 ml), dried over magnesium sulfate, filtered, and concentrated under reduced pressure. The residue was purified by column chromatography (15% ethyl acetate-hexane) to give the title compound (230 mg, Yield 35%).
$^1$H-NMR (400 MHz, CDCl$_3$) δ 7.60 (d, 1H), 7.31 (m, 2H), 7.12 (m, 1H), 4.29 (m, 2H), 3.98 (d, 1H), 3.94 (s, 3H), 3.40 (d, 1H), 2.47 (s, 3H), 2.08 (m, 2H), 1.34 (t, 3H), 1.04 (t, 3H)
Mass: M+H 315

Example 22 t-Butyl (3S)-3-({[3-(1,3-dimethyl-1H-indol-2-yl)-5-ethyl-4,5-dihydro-5-isoxazolyl]carbonyl}amino)-4-oxo-5-(2,3,5,6-tetrafluorophenoxy)pentanoate (Ik)

The compounds of Preparations 17 and 10 were reacted according to the same procedure as Preparation 4 and Example 1 to give the title compound.
$^1$H-NMR (400 MHz, CDCl$_3$) δ 7.85-7.79 (m, 1H), 7.57 (m, 1H), 7.37-7.26 (m, 2H), 7.13 (m, 1H), 6.75-6.49 (m, 1H), 5.12-4.90 (m, 3H), 3.95 (two d, 1H), 3.89 (two s, 3H), 3.45 (two d, 1H), 3.03-2.79 (m, 2H), 2.44 (two s, 3H), 2.22 (m, 1H), 2.01 (m, 1H), 1.58 & 1.37 (two s, 9H), 1.05 (two t, 3H)

Example 23

(3S)-3-({[3-(1,3-dimethyl-1H-indol-2-yl)-5-ethyl-4,5-dihydro-5-isoxazolyl]carbonyl}amino)-4-oxo-5-(2,3,5,6-tetrafluorophenoxy)pentanoic acid (Ill)

The compound of Example 22 was reacted according to the same procedure as Example 2 to give the title compound.
$^1$H-NMR (400 MHz, DMSO-d$_6$) δ 8.67 (br, 1H), 7.61-7.43 (m, 3H), 7.27 (m, 1H), 7.08 (m, 1H), 5.20 (br, 2H), 4.83 (m, 1H), 3.84 (two s, 3H), 3.76 (two d, 1H), 3.59 (two d, 1H), 2.91-2.60 (m, 2H), 2.50 (two s, 3H), 2.07-1.91 (m, 2H), 0.95 (two t, 3H)

Example 24 t-Butyl 3-({[3-(1,3-dimethyl-1H-indol-2-yl)-5-ethyl-4,5-dihydro-5-isoxazolyl]carbonyl}amino)-5-fluoro-4-oxopentanoate (Il)

The compound of Preparation 17 and t-butyl 3-amino-5-fluoro-4-hydroxypentanoate were reacted according to the same procedure as Preparation 4 and Example 1 to give the title compound.
$^1$H-NMR (400 MHz, CDCl$_3$) δ 7.79 (m, 1H), 7.60 (m, 1H), 7.32 (m, 2H), 7.13 (m, 1H), 5.20-4.90 (m, 3H), 3.97-3.89 (m, 4H), 3.46 (two d, 1H), 3.03-2.77 (m, 2H), 2.21 (m, 1H), 2.01 (m, 1H), 1.46 & 1.38 (two s, 9H), 1.05 (two t, 3H)

Example 25

3-({[3-(1,3-Dimethyl-1H-indol-2-yl)-5-ethyl-4,5-dihydro-5-isoxazolyl]carbonyl}amino)-5-fluoro-4-oxopentanoic acid (Imm)

The compound of Example 24 was reacted according to the same procedure as Example 2 to give the title compound.
$^1$H-NMR (400 MHz, DMSO-d$_6$) δ 8.68 (br, 1H), 7.60 (m, 1H), 7.45 (m, 1H), 7.26 (m, 1H), 7.07 (m, 1H), 5.20 (br, 2H), 4.81 (m, 1H), 3.84 (two s, 3H), 3.76 (two d, 1H), 3.59 (two d, 1H), 2.94-2.59 (m, 2H), 2.38 (two s, 3H), 2.07-1.91 (m, 2H), 0.95 (two t, 3H)
Mass: M+H 418

Preparation 18

Ethyl 5-ethyl-3-(1-naphthylmethyl)-4,5-dihydro-5-isoxazolecarboxylate (VIj)

1-Naphthylacetaldehyde and ethyl 2-ethylacrylate were reacted according to the same procedure as Preparations 1, 2, and 3 to give the title compound.
$^1$H-NMR (500 MHz, CDCl$_3$) δ 8.1-8.0 (d, J=8 Hz, 1H), 7.8 (d, J=7.6 Hz, 1H,), 7.8-7.7 (d, J=8 Hz, 1H), 7.5-7.4 (m, 2H), 7.4-7.3 (m, 2H), 4.1-4.0 (m, 4H), 3.1 (d, J=17.6 Hz, 1H), 2.6 (d, J=17.6 Hz, 1H), 1.8-1.7 (m, 2H), 1.2 (t, 3H), 0.7 (t, 3H)

Example 26 t-Butyl (3S)-3-({[5-ethyl-3-(1-naphthylmethyl)-4,5-dihydro-5-isoxazolyl]carbonyl}amino)-4-oxo-5-(2,3,5,6-tetrafluorophenoxy)pentanoate (Im)

The compounds of Preparations 18 and 10 were reacted according to the same procedure as Preparation 4 and Example 1 to give the title compound.
$^1$H-NMR (400 MHz, CDCl$_3$) δ 8.0 (m, 1H), 7.8 (m, 1H), 7.8 (m, 1H), 7.7 (m, 1H), 7.5 (m, 2H), 7.4-7.3 (m, 2H), 6.7 (m, 1H), 5.0-4.9 (m, 2H), 4.9-4.8 (m, 1H), 4.2-4.0 (m, 2H), 3.1 (dd, J=24.8 Hz, 1H), 2.9-2.6 (m, 3H), 1.9 (m, 1H), 1.7 (m, 1H), 1.4 (two s, 9H), 0.8 (m, 3H)

Example 27

(3S)-3-({[5-ethyl-3-(1-naphthylmethyl)-4,5-dihydro-5-isoxazolyl]carbonyl}amino)-4-oxo-5-(2,3,5,6-tetrafluorophenoxy)pentanoic acid (Inn)

The compound of Example 26 was reacted according to the same procedure as Example 2 to give the title compound.
$^1$H-NMR (400 MHz, DMSO-d$_6$) δ 12.3 (br, 1H), 8.4 (br, 1H), 8.0 (m, 1H), 7.9 (m, 1H), 7.8 (m, 1H), 7.5-7.4 (m, 5H), 5.0 (br, 2H), 4.7 (m, 1H), 4.0 (s, 2H), 3.3 (m, 1H), 3.1 (m, 1H), 2.8 (m, 2H), 2.5 (m, 1H), 1.8 (m, 1H), 1.7 (m, 1H), 0.8 (m, 3H)
MS [M+H]$^+$ 561

Example 28

(3S)-5-(t-butoxy)-3-[({5-ethyl-3-[2-(1-naphthyl)ethyl]-4,5-dihydro-5-isoxazolyl}carbonyl)amino]-2,5-dioxopentyl 2,6-dichlorobenzoate (In)

1-Naphthylpropionaldehyde and the compound of Preparation 6 were reacted according to the same procedure as Preparations 1, 2, 3, and 4, and Example 1 to give the title compound.
$^1$H-NMR (400 MHz, CDCl$_3$) δ 8.00 (d, 1H), 7.85 (m, 1H), 7.76 (m, 2H), 7.57-7.28 (m, 7H), 7.34-7.27 (m, 3H), 5.20-5.05 (m, 2H), 4.94 & 4.88 (two m, 1H), 3.39-3.27 (m, 3H), 2.97-2.72 (m, 5H), 2.07 (m, 1H), 1.86 (m, 1H), 1.46 & 1.45 (two s, 9H), 1.00 & 0.96 (two t, 3H)

Example 29

(3S)-5-[(2,6-dichlorobenzoyl)oxy]-3-[({5-ethyl-3-[2-(1-naphthyl)ethyl]-4,5-dihydro-5-isoxazolyl}carbonyl)amino]-4-oxopentanoic acid (Ioo)

The compound of Example 28 was reacted according to the same procedure as Example 2 to give the title compound.
$^1$H-NMR (400 MHz, DMSO-d$_6$) δ 8.45 (bd, 1H), 8.06 (d, 1H), 7.90 (d, 1H), 7.77 (d, 1H), 7.60-7.37 (m, 7H), 5.21-5.03 (m, 2H), 4.73 (m, 1H), 3.06 (m, 2H), 2.65 (bd, 4H), 1.91 & 1.74 (two m, 2H), 0.84 (m, 3H)

Preparation 19

Ethyl 5-ethyl-3-[(1-naphthyloxy)methyl]-4,5-dihydro-5-isoxazole Carboxylate (VII)

2-Nitroethanol pyranyl derivative (see *Synthesis*, 1993, 12, 1206-1208) and ethyl 2-ethylacrylate were reacted and the resulting product was deprotected to give ethyl 5-ethyl-(3-hydroxymethyl)-4,5-dihydro-5-isoxazolecarboxylate (23%). This compound was subjected to bromination (CBr$_4$, PPh$_3$, 94%) and then reacted with 1-naphthol (NaH, DMF, 82%) to give the title compound.
$^1$H-NMR (500 MHz, CDCl$_3$) δ 8.20 (m, 1H), 7.81 (d, 1H), 7.55-7.42 (m, 3H), 7.36 (m, 1H), 6.88 (d, 1H), 5.01 (dd, 2H), 4.22 (m, 2H), 3.61 (d, 1H), 3.07 (d, 1H), 1.97 (m, 2H), 1.27 (t, 3H), 0.93 (t, 3H)

Example 30

(3S)-3-[({5-Ethyl-3-[(1-naphthyloxy)methyl]-4,5-dihydro-5-isoxazolyl]carbonyl)amino]-4-oxo-5-(2,3,5,6-tetrafluorophenoxy)pentanoic acid (Ipp)

The compounds of Preparations 19 and 10 were reacted according to the same procedure as Preparation 4 and Examples 1 and 2 to give the title compound.
$^1$H-NMR (400 MHz, DMSO-d$_6$) δ 8.51 (br, 1H), 8.13 (m, 1H), 7.87 (m, 1H), 7.54-7.38 (m, 5H), 7.02 (m, 1H), 5.18-4.97 (m, 4H), 4.71 (m, 1H), 3.58 (two d, 1H), 3.21 (two d, 1H), 2.68 (m, 2H), 1.97 (m, 1H), 1.81 (m, 1H), 0.86 (two t, 3H)
Mass: M+H 577

Example 31

(3S)-3-{[(3-{[(4-Chloro-1-naphthyl)oxy]methyl}-5-ethyl-4,5-dihydro-5-isoxazolyl)carbonyl]amino}-4-oxo-5-(2,3,5,6-tetrafluorophenoxy)pentanoic acid (Iqq)

The bromo derivative obtained as an intermediate during the process of Preparation 19 and 4-chloro-1-naphthol were reacted according to the same procedure as Preparation 19 to give ethyl 5-ethyl-3-[(4-chloro-1-naphthyloxy)methyl]-4,5-dihydro-5-isoxazolecarboxylate, which was then reacted according to the same procedure as Preparation 4 and Examples 1 and 2 to give the title compound.
$^1$H-NMR (400 MHz, DMSO-d$_6$) δ 8.65 (m, 1H), 8.24-8.09 (m, 2H), 7.78-7.35 (m, 4H), 7.06 (m, 1H), 5.17-5.07 (m, 4H), 4.82-4.69 (m, 1H), 3.45 (two d, 1H), 3.23 (two d, 1H), 2.83-2.52 (m, 2H), 1.96-1.79 (m, 2H), 0.86 (two t, 3H)
Mass: M+H 611

Preparation 20 tert-Butyl (3S)-3-amino-4-hydroxybutanoate

To N-benzyloxycarbonyl-β-t-butylaspartic acid (3.0 g, 9.28 mmol) and NMM (1.12 ml, 1.1 Eq) was added dry tetrahydrofuran (20 ml) under nitrogen atmosphere. The reaction solution was kept at 0□. Isobutyl chloroformate (1.26 ml, 1.05 Eq) was added, and the mixture was stirred for about 40 minutes. Thus obtained slurry was filtered under nitrogen, and the resulting solution was added to NaBH$_4$ (702 mg, 2.0 Eq) solution [methanol (10 ml)-dry tetrahydrofuran (20 ml)] at −78□. The resulting mixture was slowly warmed to room temperature (two hours). The reaction was stopped by acetic acid (2.3 ml), and the reaction solution was distilled under reduced pressure to remove methanol. The residue was extracted with ethyl acetate (50 ml×2), washed with water and aqueous sodium chloride solution, dried (anhydrous Na$_2$SO$_4$), concentrated under reduced pressure, and separated-purified by column chromatography (ethyl acetate-hexane, 1:5) to give an alcohol compound (2.52 g, Yield 88%).
The benzyloxycarbonyl group of the compound obtained above was removed (Pd/C) under hydrogen balloon for one hour to give the title compound (Yield 100%).
$^1$H-NMR (400 MHz, DMSO-d$_6$) δ 4.60 (bs, 1H), 3.21 (m, 2H), 2.96 (m, 1H), 2.41 (dd, 1H), 2.03 (dd, 1H), 1.40 (s, 9H)

Preparation 21 tert-Butyl (3S)-4-hydroxy-3-({[(5R)-5-isopropyl-3-(1-isoquinolinyl)-4,5-dihydro-5-isoxazolyl]carbonyl}amino)butanoate (XVI)

The compound of Preparation 14 was reacted according to the same procedure as Preparation 4 to give an active carboxylic acid derivative (VIIf). A mixture of said active carboxylic acid derivative (VIIf, 224 mg, 0.79 mmol), the amino alcohol derivative prepared in Preparation 20 (166 mg, 1.2 Eq) and HATU (390 mg, 1.3 Eq) was cooled to 0□, triethylamine (0.33 ml, 3.0 Eq) was added in a solvent of DMF (5 ml), and the resulting mixture was reacted for two hours. The solvent was distilled under reduced pressure, and the residue was extracted with ethyl acetate (50 ml×2), washed with water, aqueous sodium bicarbonate solution, and aqueous sodium chloride solution, dried (anhydrous Na$_2$SO$_4$), concentrated under reduced pressure, and purified by column chromatography (60-70% EA/Hex) to give the title compound (330 mg, Yield 95%).

$^1$H-NMR (400 MHz, CDCl$_3$) δ 9.16 (d, 1H), 8.55 (d, 1H), 7.85 (d, 1H), 7.73-7.70 (m, 3H), 7.56 (NH, d, 1H), 4.26 (m, 1H), 4.12 (d, 1H), 4.04 (d, 1H), 3.79 (d, 1H), 3.75 (t, 2H), 2.94 (bs, 1H), 2.57 (m, 2H), 2.41 (m, 1H), 1.10 & 1.07 (two d, 6H)

Example 32

6-(tert-Butyl) 1-ethyl(2E,4S)-4-({[(5R)-5-isopropyl-3-(1-isoquinolinyl)-4,5-dihydro-5-isoxazolyl]carbonyl}amino)-2-hexenedioate (Iq)

To the compound of Preparation 21 (107 mg, 0.24 mmol) and Dess-Martin reagent (153 mg, 1.5 Eq) was added dry dichloromethane (4 ml), and the mixture was stirred for one hour at room temperature and concentrated under reduced pressure. To the residue were added dry THF (3 ml) and (carboethoxymethylene)triphenylphosphorane) (108 mg, 1.3 Eq), and the mixture was refluxed for two hours. The reaction mixture was extracted with ethyl acetate (20 ml×2), washed with water, saturated aqueous sodium bicarbonate solution and aqueous sodium chloride solution, dried (anhydrous Na$_2$SO$_4$), concentrated under reduced pressure, and preliminarily purified by prep-chromatography (40% ethyl acetate-hexane) to give the title compound (98 mg, 80%) with the diastereomer ratio of 3:1.

$^1$H-NMR (500 MHz, CDCl$_3$) of major isomer δ 9.15 (d, 1H), 8.54 (d, 1H), 7.86 (d, 1H), 7.74-7.62 (m, 4H), 6.93 (dd, 1H), 6.00 (dd, 1H), 4.98 (m, 1H), 4.19 (qt, 2H), 4.02 (d, 1H), 3.81 (d, 1H), 2.58 (m, 2H), 2.43 (m, 1H), 1.36 (s, 9H), 1.27 (t, 3H), 1.07 & 1.06 (two d, 6H)

Example 33

(3S,4E)-6-ethoxy-3-({[(5R)-5-isopropyl-3-(1-isoquinolinyl)-4,5-dihydro-5-isoxazolyl]carbonyl}amino)-6-oxo-4-hexenoic Acid (Irr)

The compound of Example 32 was reacted according to the same procedure as Example 2 to give the title compound.

$^1$H-NMR (500 MHz, MeOD-d$_3$) of major isomer δ 9.04 (d, 1H), 8.61 (d, 1H), 8.52 (d, 1H), 7.95 (d, 1H), 7.81-7.68 (m, 3H), 6.94 (dd, 1H), 6.00 (dd, 1H), 5.01 (m, 1H), 4.17 (qt, 2H), 3.90 (d, 1H), 3.82 (d, 1H), 2.71 (d, 2H), 2.39 (septet, 1H), 1.26 (t, 3H), 1.07 & 1.06 (two d, 6H)

MS: M+H 454

Example 34 tert-Butyl (3S,4E)-3-({[(5R)-5-isopropyl-3-(1-isoquinolinyl)-4,5-dihydro-5-isoxazolyl]carbonyl}amino)-5-(methylsulfonyl)-4-pentenoate (Ir)

Anhydrous dichloromethane (4 ml) was added to the compound of Example 21 (109 mg, 0.25 mmol) and Dess-Martin reagent (157 mg, 1.5 Eq), and the mixture was stirred for one hour at room temperature and concentrated under reduced pressure. The reaction was stopped by isopropyl alcohol (0.5 ml). The solid was removed by filtration under reduced pressure using Celite. The filtrate was extracted with ethyl acetate (20 ml×2), washed with water, saturated aqueous sodium bicarbonate solution, and aqueous sodium chloride solution, dried (anhydrous Na$_2$SO$_4$), and concentrated under reduced pressure to give an aldehyde compound (540 mg, Yield 99%).

Diethyl methylsulfonomethanephosphonate (113 mg, 2.0 Eq, *Synthesis*, 1969, 170) was dissolved in THF (3 ml), NaH (60% in mineral oil, 20 mg, 2.0 Eq) and above obtained aldehyde compound were added, and the mixture was refluxed for two hours. After extraction by ethyl acetate (20 ml×2), the extract was washed with water, saturated aqueous sodium bicarbonate solution, and aqueous sodium chloride solution, dried (anhydrous Na$_2$SO$_4$), concentrated under reduced pressure, and purified by prep-chromatography (60% ethyl acetate/hexane) to give the title compound (52 mg, 41%) with the diastereomer ratio of 4:1.

$^1$H-NMR (500 MHz, CDCl$_3$) of major diastereomer δ 9.14 (d, 1H), 8.55 (d, 1H), 7.86 (d, 1H), 7.76-7.65 (m, 4H), 6.92 (dd, 1H), 6.57 (dd, 1H), 5.03 (m, 1H), 4.02 (d, 1H), 3.81 (d, 1H), 2.94 (s, 3H), 2.61 (m, 2H), 2.41 (septet, 1H), 1.36 (s, 9H), 1.10 & 1.08 (two set of d, 6H)

Example 35

(3S,4E)-3-({[(5R)-5-isopropyl-3-(1-isoquinolinyl)-4,5-dihydro-5-isoxazolyl]carbonyl}amino)-5-(methylsulfonyl)-4-pentenoic acid (Iss)

The compound of Example 34 was reacted according to the same procedure as Example 2 to give the title compound.

$^1$H-NMR (500 MHz, MeOD-d$_3$) of major isomer δ 9.04 (d, 1H), 8.52 (d, 1H), 7.95 (d, 1H), 7.82-7.69 (m, 3H), 6.90 (dd, 1H), 6.71 (dd, 1H), 5.06 (m, 1H), 3.86 (m, 2H), 2.98 (s, 3H), 2.76 (d, 2H), 2.39 (m, 1H), 1.08 & 1.06 (two set of d, 6H)

MS:M+H 460

Preparation Method of Examples 36-42

The compounds which were obtained by reacting (iso)quinolinealdehyde (or 1- or 2-naphthaldehyde) and ethyl 2-ethyl acrylate (or ethyl 2-propyl acrylate) according to the same procedure as Preparations 1, 2 and 3 (or Preparations 1 and 16) were purified, if necessary, by prep-HPLC using chiral OD column to isolate active chiral isomers. The isolated active chiral isomers or inactive chiral isomers were hydrolyzed according to the same procedure as Preparation 4, and the resulting compounds were reacted with t-butyl 3-amino-5-fluoro-4-hydroxypentanoate according to the same procedure as Examples 1 and 2 to give the title compounds of following Examples 36-42.

Example 36

5-Fluoro-3-({[(5S)-3-(1-isoquinolinyl)-5-propyl-4,5-dihydro-5-isoxazolyl]carbonyl}amino)-4-oxopentanoic acid) (Itt)

$^1$H-NMR (500 MHz, DMSO-d$_6$) δ 9.02 (t, 1H), 8.61 (m, 2H), 8.08 (d, 1H), 7.96 (m, 1H), 7.85 (t, 1H), 7.78 (m, 1H), 5.05 (bs, 2H), 4.73 (m, 1H), 3.97-3.92 (dd, 1H), 3.70-3.65 (two d, 1H), 2.90-2.70 (two m, 2H), 2.03 (m, 1H), 1.91 (m, 1H), 1.48 (m, 1H), 1.32 (m, 1H), 0.93 (m, 3H)

Mass: M+H 416

Example 37

(3-({[(5S)-5-ethyl-3-(1-naphthyl)-4,5-dihydro-5-isoxazolyl]carbonyl}amino)-5-fluoro-4-oxopentanoic acid) (Iuu)

$^1$H-NMR (500 MHz, DMSO-d$_6$) δ 8.84 (s, 1H), 8.59 (bs, 1H), 8.02 (m, 2H), 7.75 (s, 1H), 7.60 (m, 3H), 5.01 (bs, 2H), 4.73 (m, 1H), 3.87-3.82 (dd, 1H), 3.70-3.65 (two d, 1H), 2.82-2.73 (two m, 2H), 2.05 (m, 2H), 1.95 (m, 1H), 0.96 (m, 3H)

Mass: M+H 401

Example 38

(3-({[(5S)-5-ethyl-3-(2-quinolinyl)-4,5-dihydro-5-isoxazolyl]carbonyl}amino)-5-fluoro-4-oxopentanoic acid) (Ivv)

$^1$H-NMR (500 MHz, DMSO-d$_6$) δ 8.61 (dd, 1H), 8.41 (m, 1H), 8.02 (m, 3H), 7.79 (t, 1H), 7.65 (t, 1H), 5.22-5.06 (m, 1H), 4.72 (m, 1H), 4.49-4.28 (m, 1H), 3.84 (m, 1H), 3.54 (m, 1H), 2.99-2.54 (two m, 2H), 2.01 (m, 1H), 1.91 (m, 1H), 0.91 (m, 3H)
Mass: M+H 402

Example 39

(3-({[(5R)-5-ethyl-3-(3-isoquinolinyl)-4,5-dihydro-5-isoxazolyl]carbonyl}amino)-5-fluoro-4-oxopentanoic Acid) (Iww)

$^1$H-NMR (400 MHz, CDCl$_3$) δ (9.25 & 9.16 (two s, 1H), 8.08~7.64 (m, 5H), 4.90-4.84 (m, 1H), 4.79-4.54 (m, 2H), 4.01-3.93 (two d, 1H), 3.54 (d, 1H), 3.03-2.87 (m, 2H), 2.27-2.19 & 2.10-2.01 (two m, 2H), 1.10-1.06 (m, 3H)
Mass: M+H 402

Example 40

3-({[5-ethyl-3-(8-quinolinyl)-4,5-dihydro-5-isoxazolyl]carbonyl}amino)-5-fluoro-4-oxopentanoic acid (Ixx)

$^1$H-NMR (500 MHz, CDCl$_3$) δ 8.98 & 8.93 (two m, 1H), 8.56-8.21 (m, 1H), 8.03-7.94 (m, 2H), 7.73 (bs, 1H), 7.60 (m, 1H), 7.53-7.48 (two m, 1H), 4.94-4.64 (m, 3H), 4.27-4.22 (two d, 1H), 3.77 (d, 1H), 3.07 & 2.92 (two m, 2H), 2.31-2.22 (m, 1H), 2.12-2.05 (m, 1H), 1.10 (t, 3H)
Mass: M+H 402

Example 41

3-({[5-ethyl-3-(3-quinolinyl)-4,5-dihydro-5-isoxazolyl]carbonyl}amino)-5-fluoro-4-oxopentanoic acid) (Iyy)

$^1$H-NMR (400 MHz, CDCl$_3$) δ 9.32 & 9.25 (two d, 1H), 8.16-8.03 (m, 2H), 7.83-7.73 (m, 3H), 7.62-7.55 (m, 1H), 4.95-4.76 (m, 3H), 3.86 (two d, 1H), 3.45-3.39 (two d, 1H), 3.17-3.01 (two m, 1H), 2.90-2.82 (m, 1H), 2.27-2.20 (m, 1H), 2.09-2.00 (m, 1H), 1.10-1.05 (m, 3H)
Mass: M+H 402

Example 42

5-Fluoro-3-({[(5R)-5-isopropyl-3-(2-quinolinyl)-4,5-dihydro-5-isoxazolyl]carbonyl}amino)-4-oxopentanoic Acid) (Izz)

$^1$H-NMR (400 MHz, CDCl$_3$) δ 8.24 (m, 1H), 8.14 (m, 1H), 8.04 (d, 1H), 7.88 (d, 1H), 7.79 (m, 1H), 7.65 (m, 1H), 7.51 (bs, 1H), 5.13-4.35 (m, 3H), 4.05-4.00 (two d, 1H), 3.73 (d, 1H), 3.05-2.82 (m, 2H), 2.42 (m, 1H), 1.10 (m, 6H)
Mass: M+H 416

Preparation Method of Examples 43-48

The compounds obtained by reacting an aromatic aldehyde (Bioorg. Med. Chem. Lett., 1996, 6, p 2173, J. Org. Chem., 1978, 43, 1372) and ethyl 2-ethyl acrylate (or ethyl 2-isopropyl acrylate) according to the same procedure as Preparations 1, 2 and 3 (or Preparations 1 and 16) were purified, if necessary, by prep-HPLC using chiral OD column to isolate active chiral isomers. The isolated active chiral isomers or inactive chiral isomers were hydrolyzed according to the same procedure as Preparation 4, and the resulting compounds were reacted with t-butyl 3-amino-5-fluoro-4-hydroxypentanoate according to the same procedure as Examples 1 and 2 to give the title compounds of following Examples 43-48.

Example 43

3-({[5-Ethyl-3-(2-isopropylphenyl)-4,5-dihydro-5-isoxazolyl]carbonyl}amino)-5-fluoro-4-oxopentanoic acid (Iaa1)

$^1$H-NMR (500 MHz, DMSO-d$_6$) δ 8.53 (bs, 1H), 7.40 (m, 2H), 7.32 (m, 1H), 7.25 (m, 1H), 5.02 (bs, 2H), 4.72 (m, 1H), 3.60-3.54 (two d, 1H), 3.46-3.43 (two d, 1H), 3.40 (m, 1H), 2.78-2.60 (two m, 2H), 1.95 (m, 1H), 1.85 (m, 1H), 1.14 (s, 6H), 0.88 (m, 3H)
Mass: M+H 393

Example 44

3-[({3-[3-(tert-Butyl)phenyl]-5-ethyl-4,5-dihydro-5-isoxazolyl}carbonyl)amino]-5-fluoro-4-oxopentanoic acid (Iaa2)

$^1$H-NMR (400 MHz, DMSO-d$_6$) δ 8.56 (dd, 1H), 7.67 (s, 1H), 7.48 (m, 1H), 7.38 (d, 2H), 5.24-5.12 (q, 1H), 4.76-4.69 (m, 1H), 4.59-4.26 (m, 1H), 3.68 (m, 1H), 3.49-3.43 (two d, 1H), 2.96-2.56 (two m, 2H), 1.98 (m, 1H), 1.85 (m, 1H), 1.29 (s, 9H), 0.89 (d, 3H)
Mass: M+H 407

Example 45

3-[({3-[4-(tert-Butyl)phenyl]-5-ethyl-4,5-dihydro-5-isoxazolyl}carbonyl)amino]-5-fluoro-4-oxopentanoic acid (Iaa3)

$^1$H-NMR (500 MHz, DMSO-d$_6$) δ 8.52 (bs, 1H), 7.58 (m, 2H), 7.43 (dd, 2H), 5.10 (bs, 2H), 4.71-4.65 (m, 1H), 3.65-3.59 (two d, 1H), 3.40-3.35 (two d, 1H), 2.86-2.60 (two m, 2H), 1.94 (m, 1H), 1.82 (m, 1H), 1.24 (s, 9H), 0.86 (m, 3H)
Mass: M+H 407

Example 46

5-Fluoro-3-({[(5R)-5-isopropyl-3-(2-isopropylphenyl)-4,5-dihydro-5-isoxazolyl]carbonyl}amino)-4-oxopentanoic Acid (Iaa4)

$^1$H-NMR (500 MHz, CDCl$_3$) δ 7.60-7.53 (m, 1H), 7.41 (m, 2H), 7.27-7.23 (m, 2H), 5.20-4.91 (m, 1H), 4.71 (m, 1H), 4.54-4.42 (m, 1H), 3.69-3.64 (two d, 1H), 3.45-3.38 (m, 2H), 3.12-2.77 (m, 2H), 2.32 (m, 1H), 1.22 (d, 6H), 1.05 (d, 6H)
Mass: M+H 407

Example 47

3-[({(5R)-3-[3-(tert-butyl)phenyl]-5-isopropyl-4,5-dihydro-5-isoxazolyl}carbonyl)amino]-5-fluoro-4-oxopentanoic acid (Iaa5)

$^1$H-NMR (500 MHz, CDCl$_3$) δ 7.69 (s, 1H), 7.48 (d, 1H), 7.41 (d, 1H), 7.35 (t, 1H), 4.74-4.50 (m, 3H), 3.69 (d, 1H), 3.40 (d, 1H), 3.06-2.77 (m, 2H), 2.32 (m, 1H), 1.33 (s, 9H), 1.04 (m, 6H)
Mass: M+H 421

Example 48

3-{[(3-[1,1'-biphenyl]-3-yl-5-isopropyl-4,5-dihydro-5-isoxazolyl)carbonyl]amino}-5-fluoro-4-oxopentanoic acid (Iaa6)

3-Biphenylcarboxaldehyde (see Synthesis, 2003, 337) was used as a starting material to give the title compound.

$^1$H-NMR (500 MHz, DMSO-$d_6$) δ 8.42 (bs, 1H), 7.87 (d, 1H), 7.73-7.69 (m, 4H), 7.52 (m, 1H), 7.45 (m, 2H), 7.38 (m, 1H), 5.03 (bs, 2H), 4.63 (m, 1H), 3.73-3.57 (m, 2H), 2.67-2.63 (two m, 2H), 2.22 (m, 1H), 0.89 (m, 6H)

Mass: M+H 441

Preparation Method of Examples 49-59

4-Substituted pyridine 2-carboxaldehydes were obtained by a method known in U.S. Pat. No. 6,043,248, JOC 1982, 47, p 4315, and they were reacted according to the same procedure as Preparations 1, 2 and 3 (or Preparations 1 and 16). The resulting compounds were purified, if necessary, by prep-HPLC using chiral OD column to isolate active chiral isomers. The isolated active chiral isomers or inactive chiral isomers were hydrolyzed according to the same procedure as Preparation 4, and the resulting compounds were reacted with t-butyl 3-amino-5-fluoro-4-hydroxypentanoate according to the same procedure as Examples 1 and 2 to give the title compounds of following Examples 49-59.

Example 49

3-({[5-Ethyl-3-(2-pyridinyl)-4,5-dihydro-5-isoxazolyl]carbonyl}amino)-5-fluoro-4-oxopentanoic Acid (Iaa7)

$^1$H-NMR (500 MHz, DMSO-$d_6$) δ 12.41 (bs, 1H), 8.61 (s, 1H), 8.59-8.53 (dd, 1H), 7.87 (m, 1H), 7.44 (m, 1H), 5.19-5.04 (two d, 1H), 4.70 (m, 1H), 4.45-4.27 (m, 1H), 3.67 (m, 1H), 3.42 (m, 1H), 2.95-2.53 (two m, 2H), 1.96 (m, 1H), 1.86 (m, 1H), 0.85 (m, 3H)

Mass: M+H 352

Example 50

3-[({3-[4-(tert-Butyl)-2-pyridinyl]-5-ethyl-4,5-dihydro-5-isoxazolyl}carbonyl)amino]-5-fluoro-4-oxopentanoic Acid (Iaa8)

$^1$H-NMR (400 MHz, CDCl$_3$) δ 8.58 (d, 1H), 7.90 (s, 1H), 7.65 (bs, 1H), 7.45-7.39 (m, 1H), 4.98-4.68 (m, 3H), 3.92 & 3.88 (two d, 1H), 3.52 & 3.47 (two d, 1H), 3.05-2.86 (m, 2H), 2.23-2.18 (m, 1H), 2.08-2.00 (m, 1H), 1.38 (s, 9H), 1.05 (t, 3H)

Mass: M+H 408

Example 51

3-[({(5R)-3-[4-(tert-butyl)-2-pyridinyl]-5-isopropyl-4,5-dihydro-5-isoxazolyl}carbonyl)amino]-5-fluoro-4-oxopentanoic acid (Iaa9)

$^1$H-NMR (400 MHz, CDCl$_3$) δ 8.58 (d, 1H), 7.88 (d, 1H), 7.61 (bs, 1H), 7.43 (m, 1H), 4.84 (m, 1H), 4.60 (bs, 2H), 3.89-3.82 (two d, 1H), 3.60-3.55 (two d, 1H), 3.04-2.86 (m, 2H), 2.38 (m, 1H), 1.38 (s, 9H), 1.07 (m, 6H)

Mass: M+H 422

Example 52

3-({[5-Ethyl-3-(4-isobutyl-2-pyridinyl)-4,5-dihydro-5-isoxazolyl]carbonyl}amino)-5-fluoro-4-oxopentanoic acid (Iaa10)

$^1$H-NMR (500 MHz, DMSO-$d_6$) δ 8.58-8.52 (dd, 1H), 8.49 (s, 1H), 7.68 (s, 1H), 7.27 (s, 1H), 5.19-5.04 (m, 1H), 4.69 (m, 1H), 4.46-4.29 (m, 1H), 3.68 (m, 1H), 3.41-3.37 (dd, 1H), 2.93-2.46 (m, 4H), 1.95-1.85 (two m, 3H), 0.86-0.82 (m, 9H)

Mass: M+H 408

Example 53

3-({[3-(4-Acetyl-2-pyridinyl)-5-ethyl-4,5-dihydro-5-isoxazolyl]carbonyl}amino)-5-fluoro-4-oxopentanoic acid (Iaa11)

$^1$H-NMR (500 MHz, CDCl$_3$) δ 8.79 (d, 1H), 8.35 (s, 1H), 7.76 (d, 1H), 7.46 (bs, 1H), 4.84-4.40 (m, 3H), 3.90-3.85 (two d, 1H), 3.51-3.46 (two d, 1H), 3.04-2.84 (m, 2H), 2.65 (s, 3H), HHHkdkdk2.16 (m, 1H), 2.02 (m, 1H), 1.03 (m, 3H)

Mass: M+H 394

Example 54

3-({[3-(4-Cyclopropyl-2-pyridinyl)-5-ethyl-4,5-dihydro-5-isoxazolyl]carbonyl}amino)-5-fluoro-4-oxopentanoic acid (Iaa12)

$^1$H-NMR (500 MHz, DMSO-$d_6$) δ 12.39 (bs, 1H), 8.41 (t, 1H), 7.56 (d, 1H), 7.12 (m, 1H), 5.19-5.04 (m, 1H), 4.72-4.66 (m, 1H), 4.46-4.27 (m, 1H), 3.69-3.63 (m, 1H), 3.39-3.35 (two d, 1H), 2.80-2.74 (m, 1H), 2.63-2.52 (m, 1H), 2.00-1.80 (m, 3H), 1.06 (m, 2H), 0.86-0.80 (m, 5H)

Mass: M+H 392

Example 55

3-({[3-(4-Cyclopentyl-2-pyridinyl)-5-ethyl-4,5-dihydro-5-isoxazolyl]carbonyl}amino)-5-fluoro-4-oxopentanoic Acid (Iaa13)

$^1$H-NMR (500 MHz, CDCl$_3$) δ 8.50 (d, 1H), 7.67 (m, 2H), 7.26 (m, 1H), 4.88-4.82 (m, 1H), 4.65 (bs, 2H), 3.88-3.81 (two d, 1H), 3.45-3.41 (two d, 1H), 3.05 (m, 1H), 2.96-2.80 (m, 2H), 2.20-2.12 (m, 3H), 2.02-1.96 (m, 1H), 1.83 (m, 2H), 1.72 (m, 2H), 1.60 (m, 2H), 1.01 (t, 3H)

Mass: M+H 420

Example 56

3-({[(5R)-3-(4-cyclopentyl-2-pyridinyl)-5-isopropyl-4,5-dihydro-5-isoxazolyl]carbonyl}amino)-5-fluoro-4-oxopentanoic Acid (Iaa14)

$^1$H-NMR (400 MHz, CDCl$_3$) δ 8.58 (m, 1H), 7.74 (d, 1H), 7.63 (bs, 1H), 7.38-7.32 (dd, 1H), 4.88-4.81 (m, 1H), 4.53 (bs, 2H), 3.87-3.79 (two d, 1H), 3.56-3.53 (two d, 1H), 3.12-3.04 (m, 1H), 3.02-2.85 (m, 2H), 2.38 (m, 1H), 2.16 (m, 2H), 1.88 (m, 2H), 1.78 (m, 2H), 1.65 (m, 2H), 1.07 (m, 6H)

Mass: M+H 434

Example 57

3-({[3-(4-Cyclohexyl-2-pyridinyl)-5-ethyl-4,5-dihydro-5-isoxazolyl]carbonyl}amino)-5-fluoro-4-oxopentanoic Acid (Iaa15)

$^1$H-NMR (400 MHz, CDCl$_3$) δ 8.61 (m, 1H), 7.75 (d, 1H), 7.64 (bs, 1H), 7.39-7.33 (dd, 1H), 4.86-4.53 (two m, 3H), 3.87 (t, 1H), 3.50-3.45 (dd, 1H), 3.05-2.85 (two m, 2H), 2.63 (m, 1H), 2.22 (m, 1H), 2.03 (m, 1H), 1.93-1.80 (two m, 5H), 1.44 (m, 5H), 1.05 (t, 3H)

Mass: M+H 434

Example 58

3-({[5-Ethyl-3-(5,6,7,8-tetrahydro-1-isoquinolinyl)-4,5-dihydro-5-isoxazolyl]carbonyl}amino)-5-fluoro-4-oxopentanoic acid (Iaa16)

$^1$H-NMR (500 MHz, DMSO-d$_6$) δ 8.60-8.53 (dd, 1H), 8.30 (d, 1H), 7.15 (d, 1H), 5.20-5.05 (m, 1H), 4.74-4.66 (m, 1H), 4.45-4.25 (m, 1H), 3.75-3.68 (m, 1H), 3.47-3.41 (m, 1H), 2.94-2.88 (m, 2H), 2.80-2.72 (m, 3H), 2.62-2.53 (m, 1H), 1.99-1.93 (m, 1H), 1.88-1.80 (m, 1H), 1.71-1.69 (m, 4H), 0.88-0.84 (m, 3H)

Mass: M+H 406

Example 59

5-Fluoro-3-({[5-isopropyl-3-(4-phenyl-2-pyridinyl)-4,5-dihydro-5-isoxazolyl]carbonyl}amino)-4-oxopentanoic Acid (Iaa17)

$^1$H-NMR (400 MHz, CDCl$_3$) δ 8.68 (d, 1H), 8.14 (s, 1H), 7.68 (m, 1H), 7.58 (m, 1H), 7.54-7.43 (m, 5H), 4.86-4.60 (m, 3H), 3.92-3.87 (two d, 1H), 3.62 (d, 1H), 3.09-2.86 (m, 2H), 2.39 (m, 1H), 1.11-1.06 (m, 6H)

Mass: M+H 442

Preparation Method of Examples 60-63

(2S)-4-(tert-butoxy)-2-({[(5R)-5-isopropyl-3-(1-isoquinolinyl)-4,5-dihydro-5-isoxazolyl]carbonyl}amino)-4-oxobutanoic acid [obtained by coupling reaction of Compound (VIIf) with Asp(O-t-Bu)-OMe and hydrolysis] was reacted according to the same procedure as Preparation 5 to give bromomethyl ketone derivative (tert-butyl (3S)-5-bromo-3-({[(5R)-5-isopropyl-3-(1-isoquinolinyl)-4,5-dihydro-5-isoxazolyl]carbonyl}amino)-4-oxopentanoate). This bromomethyl ketone derivative was reacted with diphenylphosphinic acid in KF/DMF (see Preparation 5) to give diphenylphosphoryloxymethyl ketone derivative, which was then reacted according to the same procedure as Example 2 to give the title compound (Compound of Example 60).

The compounds of following Examples 61-63 were obtained from 1-phenyl-3-(trifluoromethyl)-1H-pyrazol-5-ol, 3-benzyl-4-hydroxy-2(5H)-furanone, or isobutyric acid according to the same procedure as above.

Example 60

(3S)-5-[(diphenylphosphoryl)oxy]-3-({[(5R)-5-isopropyl-3-(1-isoquinolinyl)-4,5-dihydro-5-isoxazolyl]carbonyl}amino)-4-oxopentanoic acid (Iaa18)

$^1$H-NMR (500 MHz, DMSO-d$_6$) δ 8.92 (m, 1H), 8.58 (m, 1H), 8.05 (m, 1H), 7.94 (m, 1H), 7.81 (m, 1H), 7.75-7.72 (m, 3H), 7.57 (m, 3H), 7.49 (m, 4H), 7.35 (m, 2H), 4.90-4.65 (two m, 3H), 3.79-3.75 (two d, 1H), 3.69-3.67 (two d, 1H), 2.65 (two m, 2H), 2.22 (m, 1H), 0.84 (m, 6H)

Mass: M+H 614

Example 61

(3S)-3-({[(5R)-5-isopropyl-3-(1-isoquinolinyl)-4,5-dihydro-5-isoxazolyl]carbonyl}amino)-4-oxo-5-{[1-phenyl-3-(trifluoromethyl)-1H-pyrazol-5-yl]oxy}pentanoic acid (Iaa19)

$^1$H-NMR (500 MHz, DMSO-d$_6$) δ 8.95 (m, 1H), 8.83 (d, 1H), 8.57 (m, 1H), 8.03 (d, 1H), 7.92 (d, 1H), 7.80 (m, 1H), 7.74 (m, 1H), 7.65 (d, 1H), 7.57 (m, 1H), 7.51-7.34 (m, 3H), 6.27 (s, 1H), 5.29-5.15 (m, 2H), 4.76 (m, 1H), 3.92-3.88 (m, 1H), 3.75-3.69 (m, 1H), 2.84-2.60 (m, 2H), 2.33 (m, 1H), 0.96 (m, 6H)

Mass: M+H 624

Example 62

(3S)-5-[(4-benzyl-5-oxo-2,5-dihydro-3-furanyl)oxy]-3-({[(5R)-5-isopropyl-3-(1-isoquinolinyl)-4,5-dihydro-5-isoxazolyl]carbonyl}amino)-4-oxopentanoic Acid (Iaa20)

$^1$H-NMR (500 MHz, DMSO-d$_6$) δ 8.97 (t, 1H), 8.58 (d, 1H), 8.04 (d, 1H), 7.92 (d, 1H), 7.81 (m, 1H), 7.73 (m, 1H), 7.23-7.07 (m, 6H), 7.51 (m, 1H), 4.79-4.65 (m, 3H), 3.92-3.87 (two d, 1H), 3.74-3.68 (two d, 1H), 2.82-2.58 (m, 2H), 2.31 (m, 1H), 0.95 (m, 6H)

Mass: M+H 586

Example 63

(3S)-5-(isobutyryloxy)-3-({[(5R)-5-isopropyl-3-(1-isoquinolinyl)-4,5-dihydro-5-isoxazolyl]carbonyl}amino)-4-oxopentanoic acid (Iaa21)

$^1$H-NMR (500 MHz, DMSO-d$_6$) δ 12.39 (bs, 1H), 8.96 (t, 1H), 8.73 (m, 1H), 8.58 (dd, 1H), 8.04 (d, 1H), 7.92 (d, 1H), 7.81 (t, 1H), 7.73 (m, 1H), 4.78 (m, 2H), 4.68 (m, 1H), 3.87 (t, 1H), 3.73-3.68 (two d, 1H), 2.79-2.60 (two m, 2H), 2.56 (m, 1H), 2.31 (m, 1H), 1.05 (d, 3H), 0.95 (m, 9H)

Mass: M+H 484

Example 64

(3S)-3-({[(5R)-5-isopropyl-3-(1-isoquinolinyl)-4,5-dihydro-5-isoxazolyl]carbonyl}amino)-4-oxo-5-hexenoic acid (Iaa22)

Weinreb amide derivative of (2S)-4-(tert-butoxy)-2-({[(5R)-5-isopropyl-3-(1-isoquinolinyl)-4,5-dihydro-5-isoxazolyl]carbonyl}amino)-4-oxobutanoic acid (condensed derivative with N,O-dimethylhydroxylamine) and vinyl magnesium bromide were reacted, and the resulting compound was reacted according to the same procedure as Example 2 to give the title compound.

$^1$H-NMR (400 MHz, DMSO-d$_6$) δ 12.27 (bs, 1H), 8.95 (t, 1H), 8.74-8.67 (two d, 1H), 8.58 (m, 1H), 8.04 (d, 1H), 7.92 (d, 1H), 7.83-7.72 (m, 2H), 6.47 (m, 1H), 6.22-6.11 (two dd, 1H), 5.71-5.62 (two dd, 1H), 4.77 (m, 1H), 3.90-3.79 (m, 1H), 3.72-3.64 (m, 1H), 2.82 (m, 1H), 2.62-2.49 (m, 1H), 2.30 (m, 1H), 0.94 (m, 6H)

Mass: M+H 410

Preparation 22 t-Butyl (3S)-3-amino-4-hydroxy-5-(2-pyridinyloxy) pentanoate (VIIIf)

The bromomethyl ketone derivative X (3.2 g, 7.93 mmol), an intermediate in Preparation 5, was dissolved in benzene (30 ml), $Ag_2CO_3$ (2.62 g, 1.2 Eq) and 2-hydroxypyridine (0.93 g, 1.2 Eq) were added, and the mixture was stirred under reflux at 80□ for 3 days. The reaction mixture was filtered through Celite, concentrated under reduced pressure, and purified by column chromatography to give 2-pyridinyloxymethyl ketone derivative (XIf) (466 mg, Yield 14%).

2-Pyridinyloxymethyl ketone derivative (XIf) (227 mg, 0.548 mmol) thus obtained was dissolved in a solvent mixture of tetrahydrofuran/methanol (3:2 v/v) (10 ml), $NaBH_4$ (43 mg, 2.0 Eq) was added at 0□, and the mixture was stirred for 30 minutes at room temperature. The reaction was stopped by saturated ammonium chloride solution, and the reaction solution was concentrated under reduced pressure. The residue was extracted with ethyl acetate, washed with water and aqueous sodium chloride solution, dried (anhydrous $Na_2SO_4$), and concentrated under reduced pressure to give Compound (XIIf) (230 mg) where the ketone group was reduced to hydroxyl group.

The benzyloxycarbonyl group of the compound prepared above was removed (Pd/C) under hydrogen balloon for 40 minutes to give the title compound (155 mg, 99%).

Preparation Method of Examples 65-66

Compound VIIf (or VIIu) and VIIIf were reacted according to the same procedure as Examples 1 and 2 to give the title compounds of Examples 65-66. Here, VIIu represents 5-ethyl-3-(2-isopropylphenyl)-4,5-dihydro-5-isoxazolecarboxylic acid.

Example 65

(3S)-3-({[(5R)-5-isopropyl-3-(1-isoquinolinyl)-4,5-dihydro-5-isoxazolyl]carbonyl}amino)-4-oxo-5-(2-pyridinyloxy)pentanoic Acid (Iaa23)

$^1$H-NMR (500 MHz, MeOH-$d_4$) δ 9.04 (d, 1H), 8.50 (d, 1H), 7.95 (d, 1H), 7.81 (d, 1H), 7.77 (t, 1H), 7.69 (t, 1H), 7.59 (m, 1H), 6.85-6.80 (m, 2H), 6.67 (bs, 1H), 5.07 (bs, 1H), 4.95 (t, 1H), 4.84 (m, 1H), 3.94-3.79 (Abq, 2H), 2.92-2.80 (m, 2H), 2.39 (m, 1H), 1.09 (m, 6H)

Mass: M+H 491

Example 66

(3S)-3-({[5-ethyl-3-(2-isopropylphenyl)-4,5-dihydro-5-isoxazolyl]carbonyl}amino)-4-oxo-5-(2-pyridinyloxy)pentanoic Acid (Iaa24)

$^1$H-NMR (500 MHz, DMSO-$d_6$) δ 8.71 (bs, 1H), 8.02-7.94 (two bs, 1H), 7.71-7.64 (m, 1H), 7.42-7.18 (m, 4H), 6.96-6.90 (two t, 1H), 6.85-6.80 (two d, 1H), 4.99 (bs, 2H), 4.86-4.78 (m, 1H), 3.58 (two d, 1H), 3.48 (two d, 1H), 3.36 (m, 1H), 2.81-2.61 (m, 2H), 2.05-1.80 (two m, 2H), 1.14-1.03 (m, 6H), 0.93-0.88 (m, 3H)

Mass: M+H 468.21

Example 67

2-{[(3S)-4-carboxy-3-({[(5R)-5-isopropyl-3-(1-isoquinolinyl)-4,5-dihydro-5-isoxazolyl]carbonyl}amino)-2-oxobutyl]oxy}-1-methylpyridinium trifluoromethanesulfonate (Iaa25)

The intermediate t-butyl ((3S)-3-({[(5R)-5-isopropyl-3-(1-isoquinolinyl)-4,5-dihydro-5-isoxazolyl]carbonyl}amino)-4-oxo-5-(2-pyridinyloxy)pentanoate (49 mg, 90 μmol) obtained after the Dess-Martin oxidation reaction in Example 65 was dissolved in dichloromethane (2 ml), methyl trifluoromethanesulfonate (1.1 Eq, 10.1 μl) was added, and the mixture was stirred for one day at room temperature. After concentration under reduced pressure, the residue was subjected to the same procedure as Example 2 to give the title compound (60 mg).

$^1$H-NMR (500 MHz, DMSO-$d_6$) δ 9.00-8.91 (m, 2H), 8.76-8.57 (m, 2H), 8.42 (m, 1H), 8.04 (m, 1H), 7.93 (m, 1H), 7.80 (m, 1H), 7.75 (m, 1H), 7.54 (m, 1H), 5.77-5.48 (m, 2H), 4.85-4.81 (m, 1H), 4.00 (s, 3H), 3.94-3.69 (m, 2H), 2.87-2.60 (m, 2H), 2.33 (m, 1H), 0.98 & 0.94 (two d, 6H)

Mass: M+505.20

Example 68

2-{[(3S)-4-carboxy-3-({[5-ethyl-3-(2-isopropylphenyl)-4,5-dihydro-5-isoxazolyl]carbonyl}amino)-2-oxobutyl]oxy}-1-methylpyridinium trifluoromethanesulfonate (Iaa26)

The intermediate t-butyl (3S)-3-({[5-ethyl-3-(2-isopropylphenyl)-4,5-dihydro-5-isoxazolyl]carbonyl}amino)-4-oxo-5-(2-pyridinyloxy)pentanoate (55 mg, 0.105 mmol) obtained after the Dess-Martin oxidation reaction in Example 66 was dissolved in dichloromethane (2 ml), methyl trifluoromethanesulfonate (1.1 Eq, 13 μl) was added, and the mixture was stirred for one day at room temperature. After concentration under reduced pressure, the residue was subjected to the same procedure as Example 2 to give the title compound (59 mg, 94%).

$^1$H-NMR (500 MHz, DMSO-$d_6$) δ 8.80-8.73 (two d, 1H), 8.65 (m, 1H), 8.45-8.38 (m, 1H), 7.56-7.51 (m, 2H), 7.43-7.31 (m, 3H), 7.24-7.12 (m, H), 5.72-5.48 (m, 2H), 4.91 (m, 1H), 4.01 & 3.99 (two s, 3H), 3.64 (two d, 1H), 3.48 (two d, 1H), 3.42 (m, 1H), 2.90-2.62 (m, 2H), 2.05-1.80 (two m, 2H), 1.15-1.03 (m, 6H), 0.93-0.88 (m, 3H).

Mass: M+482.17

Preparation Method of Examples 69-70

Oxime derivative of 5-chloro-1-methyl-1H-indol-2-aldehyde or 1,5-dimethyl-1H-indol-2-aldehyde was reacted with t-butyl 3-amino-5-fluoro-4-hydroxypentanoate according to the same procedure as Preparations 1, 17, 4 and Examples 1, 2 to give the title compounds of Examples 69-70.

Example 69

3-({[3-(5-chloro-1-methyl-1H-indol-2-yl)-5-isopropyl-4,5-dihydro-5-isoxazolyl]carbonyl}amino)-5-fluoro-4-oxopentanoic acid (Iaa27)

$^1$H-NMR (500 MHz, CDCl$_3$) δ 7.59 (s, 1H), 7.46-7.39 (two d, 1H), 7.30-7.23 (m, 3H), 5.01 (m, 1H), 4.75-4.46 (m, 2H), 4.02 (d, 1H), 3.95 (s, 3H), 3.71 (d, 1H), 2.95 (m, 1H), 2.77 (m, 1H), 2.35 (m, 1H), 1.04 (m, 6H)

Mass: M+H 452

Example 70

3-({[3-(1,5-dimethyl-1H-indol-2-yl)-5-isopropyl-4, 5-dihydro-5-isoxazolyl]carbonyl}amino)-5-fluoro-4-oxopentanoic Acid) (Iaa28)

$^1$H-NMR (500 MHz, CDCl$_3$) δ 7.48 (bs, 1H), 7.39 (d, 1H), 7.23-7.14 (m, 3H), 4.76 (m, 1H), 4.70-4.50 (m, 2H), 4.07-4.02 (two d, 1H), 3.99, 3.94 & 3.93 (three s, 3H), 3.75-3.48 (m, 1H), 2.94-2.82 (two m, 1H), 2.46-2.43 (two s, 3H), 2.34 (m, 1H), 1.05 (m, 6H)
Mass: M+H 432

Preparation 23

Resolution of (5R)-5-isopropyl-3-(1-isoquinolinyl)-4,5-dihydro-5-isoxazole Carboxylic Acid 5-Isopropyl-3-(1-isoquinolinyl)-4,5-dihydro-5-isoxazolecarboxylic acid was dissolved in acetone (190 ml) by heating at 60° C., and (S)-α-methyl-benzylamine (14.5 Mt, 112 mmol) was added. The reaction mixture was cooled to room temperature and stirred for 4 hours. The resulting precipitate was filtered and washed three times by acetone (40 ml).

Thus obtained (S)-α-methyl-benzylamine salt of (5R)-5-isopropyl-3-(1-isoquinolinyl)-4,5-dihydro-5-isoxazolecarboxylic acid was dissolved in the mixture (150 ml) of acetone and water (4:1) by heating at 90° C., cooled to room temperature, and stirred for 3 hours. The resulting precipitate was filtered and washed by acetone (40 ml) three times to give pure (S)-α-methyl-benzylamine salt of (5R)-5-isopropyl-3-(1-isoquinolinyl)-4,5-dihydro-5-isoxazolecarboxylic acid (12.8 g, 24.3%, 99.8% ee).

The optical purity of (5R)-5-isopropyl-3-(1-isoquinolinyl)-4,5-dihydro-5-isoxazolecarboxylic acid was estimated by using ChiralCel OD column (4.6×250 mm, 5 μm). The mixture of n-hexane/isopropanol/trifluoroacetic acid (92/8/0.1) was used as the mobile phase at the flow rate of 1 ml/min, the column temperature was 40° C., and the detection wavelength was 225 nm. The two optical isomers were observed at the retention times of 7.8 min (R isomer) and 21.1 min (S isomer), respectively.

Example 71

Resolution of Compound (Iii-1)

1) Isolation of the SEED Compound

The two diastereomers of Example 16 were separated by using preparative liquid chromatography silica column (diameter 40 mm, DYNAMAX-100 Å). The mixture of n-hexane/ethanol/trifluoroacetic acid (4000/32/2) was used as the mobile phase at the flow rate of 50 ml/min, and the desired diastereomer was collected with the ratio of 99:1 during the retention time of 62~66 min at the detection wavelength of 227 nm (the two diastereomers were broadly eluted with the continuously changed ratio until 86 min). Thus obtained diastereomer of the 99:1 ratio was deprotected and used as the seed for the resolution.

The optical purity was estimated by using Atlantis C$_{18}$ column (4.6×250 mm, 5 μm). The mixture of acetonitrile/water/trifluoroacetic acid was used as the mobile phase at the flow rate of 1 ml/min according to the following gradient:

t=0 min, 0:100:0.1
3 min, 20:80:0.1
50 min, 100:0:0.1

Under the detection wavelength of 227 nm, the two optical isomers were observed at the retention times of 36.6 min (3R, 5R isomer) and 37.1 min (3S, 5R isomer), respectively.

(3S, 5R isomer): tert-butyl (3S)-5-fluoro-3-({[(5R)-5-isopropyl-3-(1-isoquinolinyl)-4,5-dihydro-5-isoxazolyl]carbonyl}amino)-4-oxopentanoate $^1$H-NMR (500 MHz, CDCl$_3$) δ 9.13 (d, 1H), 8.55 (d, 1H), 7.85 (d, 1H), 7.78-7.65 (m, 4H), 5.22-5.02 (two m, 2H), 4.90 (m, 1H), 4.02 (d, 1H), 3.80 (d, 1H), 2.92-2.88 (dd, 1H), 2.79-2.75 (dd, 1H), 2.41 (m, 1H), 1.34 (s, 9H), 1.09 (m, 6H)
Mass: M+H 472

(3R, 5R isomer): tert-butyl (3R)-5-fluoro-3-({[(5R)-5-isopropyl-3-(1-isoquinolinyl)-4,5-dihydro-5-isoxazolyl]carbonyl}amino)-4-oxopentanoate $^1$H-NMR (400 MHz, CDCl$_3$) δ 9.14 (d, 1H), 8.56 (d, 1H), 7.87 (d, 1H), 7.77-7.64 (m, 4H), 5.25-5.00 (two q, 2H), 4.90 (m, 1H), 4.03 (d, 1H), 3.82 (d, 1H), 2.93 (dd, 1H), 2.77 (dd, 1H), 2.42 (m, 1H), 1.35 (s, 9H), 1.11 (m, 6H)
Mass: M+H 472

(3S)-5-fluoro-3-({[(5R)-5-isopropyl-3-(1-isoquinolinyl)-4,5-dihydro-5-isoxazolyl]carbonyl}amino)-4-oxopentanoic acid (Iii-1)

$^1$H-NMR (400 MHz, CDCl$_3$) δ 9.07 (d, 1H), 8.57 (d, 1H), 7.89 (d, 1H), 7.78-7.69 (m, 3H), 7.69 (d, 1H), 4.88-4.79 (m, 2H), 4.67 (bs, 1H), 4.07 (d, 1H), 3.81 (d, 1H), 3.08-2.93 (m, 1H), 2.91-2.82 (m, 1H), 2.43 (m, 1H), 1.12 (m, 6H)
Mass: M+H 416

(3R)-5-fluoro-3-({[(5R)-5-isopropyl-3-(1-isoquinolinyl)-4,5-dihydro-5-isoxazolyl]carbonyl}amino)-4-oxopentanoic acid (Iii-2)

$^1$H-NMR (500 MHz, CDCl$_3$) δ 9.07 (d, 1H), 8.55 (d, 1H), 7.87 (d, 1H), 7.75-7.68 (m, 3H), 7.52 (bs, 1H), 5.20-4.35 (m, 3H), 4.02 (d, 1H), 3.80 (d, 1H), 3.13-2.90 (m, 2H), 2.39 (m, 1H), 1.08 (m, 6H)
Mass: M+H 416

2) Recrystallization (3S)-5-fluoro-3-({[(5R)-5-isopropyl-3-(1-isoquinolinyl)-4,5-dihydro-5-isoxazolyl]carbonyl}amino)-4-oxopentanoic acid (Iii-1)

Crude t-butyl 5-fluoro-3-({[(5R)-5-isopropyl-3-(1-isoquinolinyl)-4,5-dihydro-5-isoxazolyl]carbonyl}amino)-4-oxopentanoate (366 g) was dissolved in methylene chloride (1.9 kg) and cooled to 0° C. Triethylsilane (235 g) and trifluoroacetic acid (1.88 kg) were added and stirred for one hour at 0° C. The reaction mixture was distilled under reduced pressure, redissolved in ethyl acetate (2.4 kg), and the pH was adjusted to 5.2 by adding 2N aqueous sodium hydroxide solution (3.1 L). The organic layer was separated and the aqueous layer was extracted once with ethyl acetate (2.4 kg). Combined organic layer was distilled under reduced pressure to remove the solvent, the resulting residue was dissolved in methyl t-butyl ether (530 g), and small amount of crystalline (3S)-5-fluoro-3-({[(5R)-5-isopropyl-3-(1-isoquinolinyl)-4, 5-dihydro-5-isoxazolyl]carbonyl}amino)-4-oxopentanoic acid was added. After stirring for 16 hours at room temperature, resulting precipitate was filtered and washed with the 9:1 mixture of methyl t-butyl ether and n-hexane (210 ml).

Thus obtained (3S)-5-fluoro-3-({[(5R)-5-isopropyl-3-(1-isoquinolinyl)-4,5-dihydro-5-isoxazolyl]carbonyl}amino)-4-oxopentanoic acid was dissolved in ethyl acetate (240 ml) by heating at 50° C., n-hexane (240 ml) was slowly added, and gradually cooled to room temperature. After stirring for 24 hours at room temperature, the resulting precipitate was filtered and washed with the 1:1 mixture of ethyl acetate and n-hexane (30 ml) to give the title compound (Iii-1, 46.0 g, 3S/3R=94/6.0). The optical purity was estimated using Luna column (4.6×250 mm, 5 μm, $C_{18}$). The mixture of acetonitrile/20 mM $NH_4OAc$ (pH 6) (30/70) was used as the mobile phase at the flow rate of 1 ml/min. Under the detection wavelength of 227 nm, the two optical isomers were observed at the retention times of 8.0 min (3R isomer) and 9.0 min (3S isomer), respectively.

Experiment 1

Determination of the Caspase Inhibitory Effect

Caspase-1 and caspase-8 known as cysteine proteases in the form of $\alpha_2\beta_2$ were expressed, purified, and activated by modifying a method known in Thornberry, N. A. et al, *Nature*, 1992, 356, 768. Thornberry, N. A. *Methods in Enzymology*, 1994, 244, 615. Walker, N. P. C. et al. *Cell*, 1994, 78, 343, and caspase-9 was also purified by a similar method, and the inhibitory activity against them was tested. Briefly describing, p10 and p20 subunits (Thornberry, N. A. et al, *Nature*, 1992, 356, 768) were expressed in *E. coli* and purified by nickel column and anionic exchange chromatography to give caspase-1, caspase-8 and caspase-9. The fluorescent substrate AcYVAD-AFC for thus obtained caspase-1, AcDEVD-AFC for caspase-8, and AcLEHD-AFC for caspase-9 were used for determining specific activity of the synthesized inhibitors. The enzyme reaction was carried out at 25° C. with various concentrations of the inhibitors in a buffer solution containing 50 mM HEPES(pH 7.50), 10% (w/v) sucrose, 0.1% (w/v) CHAPS, 100 mM NaCl, 1 mM EDTA, and 10 mM DTT in the presence of 50 μM AcYVAD-AFC for 10 nM caspase-1, 50 μM AcDEVD-AFC for 2.1 nM caspase-8, and 150 μM AcLEHD-AFC for 200 nM caspase-9. The inhibitory constants $K_i$ and $K_{obs}$ of the inhibitors were determined by measuring the reaction velocity with the time lapse using a fluorescent spectrometer and by obtaining the initial rate constant. $K_i$ was calculated from the Lineweaver Burk Plot, and $K_{obs}$ from the following Equation 1.

$$K_{obs} = -\ln(1 - A_t/A_{oo})/t \qquad \text{Equation 1}$$

in which $A_t$ means cleavate rate (%) at time t, and $A_{oo}$ means the maximum cleavage rate (%).

Spectra MAX GeminiXS Fluorescent Spectrometer of Molecular Device Co. was used at the excitation wavelength of 405 nm and the emission wavelength of 505 mm.

The in vivo inhibitory activity of the inhibitors was determined by subjecting Jurkat cell (ATCC TIB-152) to apoptosis using Fas antibody (Upstate Biotech 05-201) and by detecting the color change according to the WST-1 method known in Francoeur A. M. and Assalian A. (1996) Biochemica 3, 19-25 to observe the amount of alive Jurkat cells when the cells were treated by the inhibitor. Spectra MAX 340 Spectrometer of Molecular Device Co. was used at the absorbance wavelength of 440 nm.

TABLE 1

| Com. No. | Caspase-1 $K_{obs}/[I]$ ($M^{-1}min^{-1}$) | Caspase-8 $K_{obs}/[I]$ ($M^{-1}min^{-1}$) | Caspase-9 $K_{obs}/[I]$ ($M^{-1}min^{-1}$) | Jurkat cell $IC_{50}$ (μM) |
|---|---|---|---|---|
| Icc | 1.9E5 | 3.3E4 | | 22.5 |
| Idd | 3.1E5 | 1.9E5 | | 4.25 |
| Iee | | 1.8E5 | | 32.6 |
| Iff | | 5.0E5 | | 1.2 |
| Igg | 2.7E6 | 1.5E6 | 3.2E5 | 0.17 |
| Iii | 1.1E6 | 1.3E7 | 2.0E5 | 0.1 |
| Iii-u* | | 1.9E5 | | 0.71 |
| Iii-1 | | 2.3E7 | | |
| Iii-2 | | 4.7E5 | | |
| Ijj | | 1.9E5 | | 4.7 |
| Ikk | | 1.2E5 | | 1.1 |
| Ill | | 1.3E5 | | 39.2 |
| Imm | | 1.6E5 | | 2.0 |
| Inn | | 2.6E5 | | 6.5 |
| Ioo | | 2.0E4 | | 50 |
| Ipp | 2.3E6 | 1.7E5 | | 3.5 |
| Iqq | 3.3E6 | 1.4E5 | | 37 |
| Irr | | | | No Activity |
| Iss | | | | No Activity |
| Itt | | 4.3E5 | | 0.16 |
| Iuu | | 2.9E5 | | 0.98 |
| Ivv | | 1.5E6 | | 0.15 |
| Iww | | 1.1E6 | | 1.9 |
| Ixx | | 4.0E4 | | 26.5 |
| Iyy | | 3.1E5 | | 31.2 |
| Izz | | 4.2E5 | | 1.25 |
| Iaa1 | | 1.8E5 | | 0.33 |
| Iaa2 | | 3.2E5 | | 0.56 |
| Iaa3 | | 1.4E5 | | 2.65 |
| Iaa4 | | 5.0E5 | | 0.67 |
| Iaa5 | | 3.0E5 | | 0.3 |
| Iaa6 | | 2.0E5 | | 2.45 |
| Iaa7 | | 4.4E4 | | 2.27 |
| Iaa8 | | 4.5E5 | | 0.70 |
| Iaa9 | | 2.3E5 | | 1.24 |
| Iaa10 | | 1.5E5 | | 1.02 |
| Iaa11 | | 6.4E4 | | 31 |
| Iaa12 | | 1.9E5 | | 0.70 |
| Iaa13 | | 3.1E5 | | 0.35 |
| Iaa14 | | 4.1E5 | | 0.79 |
| Iaa15 | | 4.3E5 | | 0.72 |
| Iaa16 | | 6.2E5 | | 0.73 |
| Iaa17 | | 1.8E5 | | 1.14 |
| Iaa18 | | 5.2E5 | | 1.5 |
| Iaa19 | | 1.6E4 | | No Activity |
| Iaa20 | | 3.7E4 | | No Activity |
| Iaa21 | | No Activity | | No Activity |
| Iaa22 | | No Activity | | |
| Iaa23 | | 2.9E4 | | No Activity |
| Iaa24 | | No Activity | | |
| Iaa25 | | 1.7E5 | | No Activity |
| Iaa26 | | 3.1E4 | | No Activity |
| Iaa27 | | 8.2E5 | | 1.3 |
| Iaa28 | | 1.8E6 | | 0.6 |

*Compound Iii-u is the (5S) form of Comound Iii.

Experiment 2

Therapeutic Effect for LPS-Induced Acute Hepatitis in Mouse

Step 1) Preparation of Blood Sample

Female Balb/c mice (6 weeks, Charles River Laboratory, Osaka, Japan) were kept under the conditions of 22□, 55% of relative humidity, and light-darkness cycle of 12 hours. Food and water were supplied ad libitum. In pyrogen-free saline were dissolved LPS (lipopolysaccharide) and D-galactosamine in concentrations of 0.4 mg/ml and 280 mg/ml, respectively, and their 1:1 mixture was injected to mice in the amount of 5 ml/kg. Immediately after the injection of LPS and D-galactosamine, vehicle (a mixture of PEG400:ethanol:Tween80=15:7.5:2.5 was diluted by five times with saline) wherein the test compound is dissolved or the vehicle alone was intraperitoneally injected into the mice. After 8 hours from the drug injection, blood samples were obtained from their hearts.

Step 2: Determination of the Activity of Plasma Aminotransferase

The plasma ALT activity was determined for the blood samples obtained in Step 1 using ALT assay kit (Asan Pharm. Co., Seoul, Korea) according to the manufacturer's instruction. As a result, it appeared that the injection of LPS and D-galactosamine steeply increases the ALT activity in plasma, and the test compounds inhibit the increased enzyme activity in a dose-dependent manner. Based on these results, $ED_{50}$ values of the test compounds were calculated using Prism software of GraphPad Co. to give 0.01-10 mg/kg.

Experiment 3

Inhibitory Effect Against Hepatic Fibrosis in SD Rats

Step 1) Induction of Hepatic Fibrosis and Administration

Male Spargue-Dawley rats (6 weeks, Korea Biolink) were kept under the conditions of 22☐, 55% of relative humidity, and light-darkness cycle of 12 hours. Food and water were supplied ad libitum. For the ligation of biliary duct, the rats were anesthetized by inhalation of 1% halothane, abdomen of the rats were cut open, the distal and proximal biliary ducts were ligated, the part between the ligation sites were cut, 2 ml of saline was injected, and sutured.

Test compound (Iii) was orally administered in a dosage of 3 mg/kg or 10 mg/kg twice a day. That is, the compound was dissolved in a cosolvent (PEG400:ethanol:Tween80=15:7.5: 2.5), diluted with phosphate buffer (pH 7.4) by five times, and administered. To the control group was administered the solution without the test compound. The administration was made for 1 week after 1 week from the ligation of biliary duct.

Step 2: Preparation of Tissue Section and Sirius Red Staining

After the administration, the rats were sacrificed. The livers were fixed by 10% neutral formalin and a paraffin section of 5 μm thickness was prepared and stained by 0.1% Sirius red (Direct red 80, Sigma). The tissue section was investigated by an optical microscope to observe the collagen fibers stained in red, and the results are represented in FIG. 1.

Experiment 4

Inhibitory Effect Against Apoptosis During the Bile Stagnation in SD Rats

The test compound (Iii) was administered to the SD rats whose biliary ducts were ligated according to the procedure as Step 1 of Experiment 3. After 2 weeks from the operation, the rats were sacrificed. The livers were fixed by 10% neutral formalin and a paraffin section of 5 μm thickness was prepared. TUNEL staining was carried out using ApopTag Peroxidase In Situ Apoptosis Detection kit (Chemicon) according to the manufacturer's instruction. More than 10 sites of the TUNEL stained liver tissue were photographed in 200 magnifications without any overlap, of which result was shown in FIG. 2. The number of cells suffering apoptosis in each test group was counted and represented in the following Table 2. In the following table, the Sham operation means the case where the biliary duct was exposed but not ligated, and the BDL operation means the case where only the vehicle was administered after the ligation of biliary duct.

TABLE 2

Inhibitory effect of compound (Iii) against hepatic cell apoptosis during the bile stagnation
(Unit: TUNEL positive cells/field)

| Sham operation | BDL operation | BDL + Compound (Iii) 3 mg/kg | BDL + Compound (Iii) 10 mg/kg |
|---|---|---|---|
| 0.76 ± 0.15 | 16.7 ± 2.75 | 4.12 ± 1.3 | 5.66 ± 1.34 |

CONCLUSION

The effective inhibition of apoptosis (75% inhibition) by Compound (Iii) was shown by TUNEL staining in a model established by the induction of hepatic fibrosis through the bile stagnation. In addition, the Sirius Red staining showed a severe fibrosis in the control group, but almost no fibrosis in the Compound (Iii) treated group. This result demonstrates the inhibitory effect of Compound (Iii) against hepatic fibrosis in rats, and so it is expected that Compound (Iii) can exhibit the pharmacological activity of suppressing liver cirrhosis by inhibiting the apoptosis of hepatic cell in clinical application. The application may be expanded not only to the hepatic cirrhosis by bile stagnation, but also to various hepatic diseases where hepatic fibrosis due to the apoptosis is included.

Experiment 5

Antiphlogistic Effect in Rats

Male SD rats (6 weeks, Orient) were kept under the conditions of 22☐, 55% of relative humidity, and light-darkness cycle of 12 hours. Food and water were supplied ad libitum. Before the induction of edema, the foot volume of each rat was measured by plethysmometer. Before the induction of edema, vehicle (a mixture of PEG400: ethanol:Tween80=15: 7.5:2.5 was diluted by ten times with phosphate buffer) wherein the test compound is dissolved or the vehicle alone was orally administered into the rats. Carrageenan (gamma) was dissolved in the concentration of 1% in saline, and subcutaneously injected into the right rear foot of the rats in the dosage of 100 μl. After 3 hours, the right foot volume was measured again by plethysmometer. The effect of the test compound was shown by edema inhibition (%) (see Table 3). The edema inhibition (%) was calculated according to the following Equation 2.

Edema Inhibition (%)=100×(Average of the increased foot volume in the vehicle-administered group−Increased foot volume in the test compound-administered group)/Average of the increased foot volume in the vehicle-administered group        Equation 2

TABLE 3

Edema inhibition effect of Compound (Iii)
Edema inhibition effect (%)

| Dosage (mg/kg) | Average | SEM |
|---|---|---|
| 3 | 2.3 | 7.7 |
| 30 | 20.7 | 9.7 |
| 100 | 22.7 | 2.6 |

Experiment 6

Therapeutic Effect for Rheumatic Arthritis in Rats

Female Lewis rats (7 weeks, Charles River, Japan) were kept under the conditions of 22□, 55% of relative humidity, and light-darkness cycle of 12 hours. Food and water were supplied ad libitum. Type II collagen (bovine) was dissolved in 0.05M acetic acid in a concentration of 2 mg/ml at 4□, and the same amount of Complete Freund's adjuvant was added to emulsify the solution at 4□. 0.1 ml of thus emulsified solution was subcutaneously injected into the rattail of the Lewis rats. After 7 days, the emulsified solution was injected again in the same manner. From the date on which the second emulsified solution was injected, vehicle (a mixture of PEG400:ethanol:Tween80=15:7.5:2.5 was diluted by ten times with phosphate buffer) wherein the test compound is dissolved or the vehicle alone was orally administered into the rats every day. On Day 14 from the first injection of the collagen-containing emulsified solution, the right rear foot volume was measured again by plethysmometer (see Table 4). The edema inhibition (%) was determined by the following Equation 3.

Edema Inhibition (%)=100×(Average of the increased foot volume in the vehicle-administered group on Day 14–Increased foot volume in the test compound-administered group on Day 14)/Average of the increased foot volume in the vehicle-administered group on Day 14    Equation 3

Further, p-value was calculated by Student t-test from the increased foot volume on Day 14 to confirm the significance.

TABLE 4

| Dosage of Compound (Iii) (mg/kg) | Foot edema inhibition effect | | | | | |
|---|---|---|---|---|---|---|
| | Foot volume (ml) | | | | Edema inhibition effect (%) | |
| | Day 0 | | Day 14 | | Day 14 | |
| | Average | SEM | Average | SEM | Average | SEM |
| 0 | 1.115 | 0.036 | 1.975 | 0.257 | — | |
| 10 | 1.134 | 0.032 | 1.394* | 0.089 | 69.8 | 10.8 |

*p-value = 0.032

In the foot edema test in rats, Compound (Iii) showed a dose-dependent edema inhibition effect of about 2, 21, and 23% at a dosage of 3, 30, and 100 mg/kg, respectively. In the model of rheumatic arthritis, the foot edema was decreased significantly (about 70% decrease) in the Compound (Iii)-administered group on Day 14 when the negative control group showed the maximum edema. Therefore, it is considered that Compound (Iii) has an inhibitory effect against the progress of inflammation in an inflammatory disease model, and so can treat the autoimmune inflammatory diseases.

Experiment 7

Effect Comparison with the Known Compound

Compound (Iii) according to the present invention and LB84068MP (Compound 68) known in PCT/KR00/01047 (WO 01/21600) were tested and the results are shown in the following Table 5.

TABLE 5

| | LB84068MP | Iii |
|---|---|---|
| $K_{obs}/[I]$ against caspase-8 | 1.02E6 ($M^{-1}min^{-1}$) | 1.30E7 ($M^{-1}min^{-1}$) |
| $IC_{50}$ (Jurkat cell) | 1.6 μM | 0.1 μM or less |
| $ED_{50}$ (LPS + Gal) | 0.99 mg/kg | 0.01 mg/kg |
| Solubility (pH = 7.44 phosphate) | 0.93 mg/ml or less | 7.8 g/ml |

As can be seen from the above Table 5, Compound (Iii) according to the present invention showed an increased inhibitory activity by 10 times or more against caspase-8 and Jurkat cell compared with LB84068MP, and by about 100 times against LPS-induced acute hepatitis model (mouse). Also, regarding the physico-chemical properties, the compound showed improved solubility, and so can be easily used as an injection. That is, the compound of the present invention shows highly more improved effects than the comparison compound of LB84068MP in both aspects of activity and physico-chemical properties.

The invention claimed is:

1. A compound of the following formula (1):

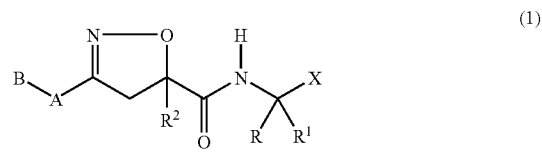

(1)

in which

I) R represents H, simple alkyl chain (-SAC), simple cycloalkyl chain (-SCAC), aryl group (—Ar), or simple alkyl chain substituted by aryl (-SAC-Ar), II) $R^1$ represents -SAC, -SCAC, —Ar, -SAC-Ar, or a side chain residue of all the natural amino acids; and the compound of formula (1) may exist in a specific diastereomeric form, or mixtures thereof when the carbon to which $R^1$ is attached becomes a stereocenter due to the $R^1$ group; or the compound of formula (1) may have a protecting group in an ester form (—$CO_2R^3$ wherein $R^3$ is -SAC) or a sulfonamide form (—$CONHSO_2R^4$ wherein $R^4$ is -SAC), or may exist in the form of pharmaceutically acceptable salt, when $R^1$ is a side chain residue of an amino acid containing carboxyl moiety; or the compound of formula (1) may also exist in the form of pharmaceutically acceptable salt when $R^1$ is a side chain residue of an amino acid containing a base moiety, III) $R^2$ represents -SAC, -SCAC, —Ar, -SAC-Ar, or a side chain residue of the natural amino acids; and the compound of formula (1) may exist in a specific diastereomeric form, or mixtures thereof when the carbon to which $R^2$ is attached becomes a stereocenter due to the $R^2$ group; the compound of formula (1) may have a protecting group in an ester form (—$CO_2R^5$ wherein $R^5$ is -SAC) or a sulfonamide form (—$CONHSO_2R^6$ wherein $R^6$ is -SAC), or may exist in the form of pharmaceutically acceptable salt, when $R^2$ is a side chain residue of an amino acid containing carboxyl moiety; or the compound of formula (1) may also exist in the form of pharmaceutically acceptable salt when $R^2$ is a side chain residue of an amino acid containing a base moiety, or $R^2$ further represents H; —$(CH_2)_nOR^7$ wherein $R^7$ is -SAC, -SCAC, —Ar, or -SAC-Ar, and n=1 or 2; or —(CH$_2$)$_n$OC(=O)R$^8$ wherein R$^8$ is -SAC, -SCAC, —Ar, or -SAC-Ar, and n=1 or 2, IV) A represents —(CH$_2$)$_n$— (n=0-4), —O—(CH$_2$)$_n$— (n=0-4), or —NR$^9$—(CH$_2$)$_n$— (n=0-4) wherein R$^9$ is -SAC, -SCAC, —Ar, or -SAC-Ar, V) B represents H, -SAC, -SCAC, —Ar, or -SAC-Ar, or VI) R and R$^1$ may form a cycle together with the carbon atom to which they are attached, where —R—R$^1$— is —(CH$_2$)$_n$—, —(CH$_2$)$_n$—O—(CH$_2$)$_m$—, or —(CH$_2$)$_n$—NR$^{10}$—(CH$_2$)$_m$— wherein n+m<9 and R$^{10}$ is -SAC, -SCAC, —Ar, -SAC-Ar, —C(=O)— SAC, —C(=O)-SCAC, —C(=O)—Ar, or —C(=O)-SAC-Ar, VII) X represents —C(=O)CH$_2$OR$^{11}$ wherein R$^{11}$ is -SAC, -SCAC, —Ar, or -SAC-Ar; —C(=O)CH$_2$OC(=O)R$^{12}$ wherein R$^{12}$ is -SAC, -SCAC, —Ar, or -SAC-Ar; —CH=CH—CO$_2$R$^{13}$ wherein R$^{13}$ is -SAC, -SCAC, —Ar, or -SAC-Ar; —CH=CH—SO$_2$R$^{14}$ wherein R$^{14}$ is -SAC, -SCAC, —Ar, or -SAC-Ar; —C(=O)CH=CH$_2$; or —COCH$_2$—W wherein W is —N$_2$, —F, —Cl, —Br, —I, —NR$^{15}$R$^{16}$ (R$^{15}$ and R$^{16}$ each are -SAC, -SCAC, —Ar, or -SAC-Ar, or together may form 3- to 6-membered saturated or unsaturated cyclic group), —SR$^{17}$ (R$^{17}$ is -SAC, -SCAC, —Ar, or —SAC-Ar), or is the following formula:

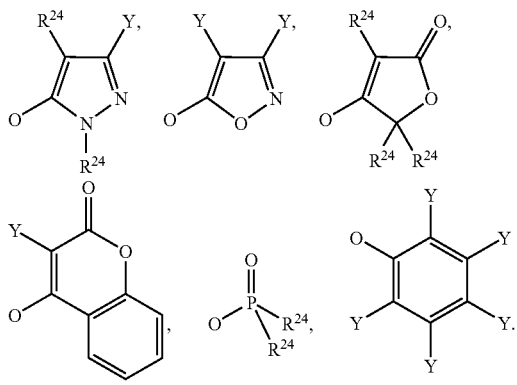

wherein
Y is H, —OH, —OR$^{18}$ (R$^{18}$=-SAC or -SCAC), —C(=O)R$^{19}$ (R$^{19}$=—H, -SAC, or -SCAC), —F, —Cl, —Br, —I, —CN, —NC, —N$_3$, —CO$_2$H, CF$_3$, —CO$_2$R$^{20}$(R$^{20}$=-SAC or —SCAC), —C(=O)NHR$^{21}$ (R$^{21}$=-SAC or -SCAC), or —C(=O)NR$^{22}$R$^{23}$ (R$^{22}$ and R$^{23}$ each are -SAC, -SCAC, —Ar, or -SAC-Ar),
R$^{24}$ is H, -SAC, -SAC-Ar, or —Ar, salt, or stereoisomer thereof.

2. The compound according to claim 1 wherein R represents H.

3. The compound according to claim 1 wherein R$^1$ represents —CH$_2$COOH, —CH$_2$COOR$^3$ (R$^3$=SAC), or —CH$_2$CONHSO$_2$R$^4$ (R$^4$=SAC).

4. The compound according to claim 1 wherein R$^2$ represents H, -SAC, —Ar, or —(CH$_2$)$_n$OR$^7$ (R$^7$=-SAC, -SCAC, —Ar, or -SAC-Ar, and n=1 or 2).

5. The compound according to claim 1 wherein X represents —C(=O)CH$_2$OAr, —C(=O)CH$_2$C(=O)Ar, or —COCH$_2$—W wherein W is —N$_2$, —F, —Cl, —Br, —I, —NR$^{15}$R$^{16}$ (R$^{15}$ and R$^{16}$ each are -SAC, -SCAC, —Ar, or -SAC-Ar, or together may form 3- to 6-membered saturated or unsaturated cyclic group), or —SR$^{17}$ (R$^{17}$ is -SAC, -SCAC, —Ar, or -SAC-Ar).

6. The compound according to claim 1 wherein
I) R represents H,
II) R$^1$ represents —CH$_2$—COOH, —CH$_2$COOR$^3$ (R$^3$=SAC), or —CH$_2$CONHSO$_2$R$^4$ (R$^4$=SAC),
III) R$^2$ represents H, -SAC, —Ar, or —(CH$_2$)$_n$OR$^7$ (R$^7$=-SAC, -SCAC, —Ar, or -SAC-Ar, and n=1 or 2),
IV) A represents —(CH$_2$)$_n$— (n=0-4) or —O—(CH$_2$)$_n$— (n=0-4),
V) B represents H, -SAC, -SCAC, —Ar, or -SAC-Ar,
VI) X represents —COCH$_2$N$_2$, —COCH$_2$F, —COCH$_2$Cl, —COCH$_2$Br, —COCH$_2$I, —COCH$_2$OAr, —COCH$_2$OCOAr or —COCH$_2$SR$^{17}$ (R$^{17}$ is -SAC, -SCAC, —Ar or -SAC-Ar).

7. The compound according to claim 1 which is selected from the following group:

(1) (3S)-5-[(2,6-dichlorobenzoyl)oxy]-3-({[5-methyl-3-phenyl-4,5-dihydro-5-isoxazolyl]carbonyl}amino)-4-oxopentanoic acid (Iaa);

(2) (3S)-3-({[5-methyl-3-phenyl-4,5-dihydro-5-isoxazolyl]carbonyl}amino)-4-oxo-5-phenoxypentanoic acid (Ibb);

(3) (3S)-3-({[5-ethyl-3-phenyl-4,5-dihydro-5-isoxazolyl]carbonyl}amino)-4-oxo-5-(2,3,5,6-tetrafluorophenoxy)pentanoic acid (Icc);

(4) (3S)-3-({[5-ethyl-3-(1-naphthyl)-4,5-dihydro-5-isoxazolyl]carbonyl}amino)-4-oxo-5-(2,3,5,6-tetrafluorophenoxy)pentanoic acid (Idd);

(5) (3S)-3-({[5-ethyl-3-(2-naphthyl)-4,5-dihydro-5-isoxazolyl]carbonyl}amino)-4-oxo-5-(2,3,5,6-tetrafluorophenoxy)pentanoic acid (Iee), (6) (3S)-3-({[5-ethyl-3-(1-isoquinolinyl)-4,5-dihydro-5-isoxazolyl]carbonyl}amino)-4-oxo-5-(2,3,5,6-tetrafluorophenoxy)pentanoic acid (Iff);

(7) 3-({[5-ethyl-3-(1-isoquinolinyl)-4,5-dihydro-5-isoxazolyl]carbonyl}amino)-5-fluoro-4-oxopentanoic acid (Igg);

(8) ethyl 3-({[5-ethyl-3-(1-isoquinolinyl)-4,5-dihydro-5-isoxazolyl]carbonyl}amino)-5-fluoro-4-oxopentanoate (Ihh);

(9) 5-fluoro-3-({[(5R)-5-isopropyl-3-(1-isoquinolinyl)-4,5-dihydro-5-isoxazolyl]carbonyl}amino)-4-oxopentanoic acid (Iii);

(10) 3-({[5-ethyl-3-(4-quinolinyl)-4,5-dihydro-5-isoxazolyl]carbonyl}amino)-5-fluoro-4-oxopentanoic acid (Ijj);

(11) 3-({[3-(benzothiophen-2-yl)-5-ethyl-4,5-dihydro-5-isoxazolyl]carbonyl}amino)-5-fluoro-4-oxopentanoic acid (Ikk);

(12) (3S)-3-({[3-(1,3-dimethyl-1H-indol-2-yl)-5-ethyl-4,5-dihydro-5-isoxazolyl]carbonyl}amino)-4-oxo-5-(2,3,5,6-tetrafluorophenoxy)pentanoic acid (Ill);

(13) 3-({[3-(1,3-dimethyl-1H-indol-2-yl)-5-ethyl-4,5-dihydro-5-isoxazolyl]carbonyl}amino)-5-fluoro-4-oxopentanoic acid (Imm);

(14) (3S)-3-({[5-ethyl-3-(1-naphthylmethyl)-4,5-dihydro-5-isoxazolyl]carbonyl}amino)-4-oxo-5-(2,3,5,6-tetrafluorophenoxy)pentanoic acid (Inn);

(15) (3S)-5-[(2,6-dichlorobenzoyl)oxy]-3-[({5-ethyl-3'-[2-(1-naphthyl)ethyl]-4,5-dihydro-5-isoxazolyl}carbonyl)amino]-4-oxopentanoic acid (Ioo);

(16) (3S)-3-[({5-ethyl-3-[(1-naphthyloxy)methyl]-4,5-dihydro-5-isoxazolyl}carbonyl)amino]-4-oxo-5-(2,3,5,6-tetrafluorophenoxy)pentanoic acid (Ipp);

(17) (3S)-3-{[(3-{[(4-chloro-1-naphthyl)oxy]methyl}-5-ethyl-4,5-dihydro-5-isoxazolyl)carbonyl]amino}-4-oxo-5-(2,3,5,6-tetrafluorophenoxy)pentanoic acid (Iqq);

(18) (3S,4E)-6-ethoxy-3-({[(5R)-5-isopropyl-3-(1-isoquinolinyl)-4,5-dihydro-5-isoxazolyl]carbonyl}amino)-6-oxo-4-hexenoic acid (Irr);

(19) (3S,4E)-3-({[(5R)-5-isopropyl-3'-(1-isoquinolinyl)-4,5-dihydro-5-isoxazolyl]carbonyl}amino)-5-(methylsulfonyl)-4-pentenoic acid (Iss);

(20) 5-fluoro-3-({[(5S)-3-isoquinolinyl)-5-propyl-4,5-dihydro-5-isoxazolyl]carbonyl}amino)-4-oxopentanoic acid (Itt);

(21) 3-({[(5S)-5-ethyl-3-(1-naphthyl)-4,5-dihydro-5-isoxazolyl]carbonyl}amino)-5-fluoro-4-oxopentanoic acid (Iuu);

(22) 3-({[(5S)-5-ethyl-3-(2-quinolinyl)-4,5-dihydro-5-isoxazolyl]carbonyl}amino)-5-fluoro-4-oxopentanoic acid (Ivv);

(23) 3-({[(5R)-5-ethyl-3-(3-isoquinolinyl)-4,5-dihydro-5-isoxazolyl]carbonyl}amino)-5-fluoro-4-oxopentanoic acid (Iww);

(24) 3-(5% [5-ethyl-3-(8-quinolinyl)-4,5-dihydro-5-isoxazolyl]carbonyl}amino)-5-fluoro-4-oxopentanoic acid (Ixx);

(25) 3-({[5-ethyl-3-(3-quinolinyl)-4,5-dihydro-5-isoxazolyl]carbonyl}amino)-5-fluoro-4-oxopentanoic acid (Iyy);

(26) 5-fluoro-3-({[(5R)-5-isopropyl-3-(2-quinolinyl)-4,5-dihydro-5-isoxazolyl]carbonyl}amino)-4-oxopentanoic acid (Izz);

(27) 3-({[5-ethyl-3-(2-isopropylphenyl)-4,5-dihydro-5-isoxazolyl]carbonyl}amino)-5-fluoro-4-oxopentanoic acid (Iaa1);

(28) 3-[3-[3-(tert-butyl)phenyl]-5-ethyl-4,5-dihydro-5-isoxazolyl}carbonyl)amino]-5-fluoro-4-oxopentanoic acid (Iaa2);

(29) 3-[({3-[4-(tert-butyl)phenyl]-5-ethyl-4,5-dihydro-5-isoxazolyl}carbonyl)amino]-5-fluoro-4-oxopentanoic acid (Iaa3);

(30) 5-fluoro-3-({[(5R)-5-isopropyl-3-(2-isopropylphenyl)-4,5-dihydro-5-isoxazolyl]carbonyl}amino)-4-oxopentanoic acid (Iaa4);

(31) 3-[({(5R)-3-[3-(tert-butyl)phenyl]-5-isopropyl-4,5-dihydro-5-isoxazolyl}carbonyl)amino]-5-fluoro-4-oxopentanoic acid (Iaa5);

(32)₃-{[(3-[1,1'-biphenyl]-3-yl-5-isopropyl-4,5-dihydro-5-isoxazolyl)carbonyl]amino}-5-fluoro-4-oxopentanoic acid (Iaa6);

(33) 3-({[5-ethyl-3-(2-pyridinyl)-4,5-dihydro-5-isoxazolyl]carbonyl}amino)-5-fluoro-4-oxopentanoic acid (Iaa7);

(34) 3-[({3-[4-(tert-butyl)-2-pyridinyl]-5-ethyl-4,5-dihydro-5-isoxazolyl}carbonyl)amino]-5-fluoro-4-oxopentanoic acid (Iaa8);

(35) 3-[({(5R)-3-[4-(tert-butyl)-2-pyridinyl]-5-isopropyl-4,5-dihydro-5-isoxazolyl]carbonyl}amino]-5-fluoro-4-oxopentanoic acid (Iaa9);

(36) 3-({[5-ethyl-3-(4-isobutyl-2-pyridinyl)-4,5-dihydro-5-isoxazolyl]carbonyl}amino)-5-fluoro-4-oxopentanoic acid (Iaa10);

(37) 3-({[3-(4-acetyl-2-pyridinyl)-5-ethyl-4,5-dihydro-5-isoxazolyl]carbonyl}amino)-5-fluoro-4-oxopentanoic acid (Iaa11);

(38) 3-({[3-(4-cyclopropyl-2-pyridinyl)-5-ethyl-4,5-dihydro-5-isoxazolyl]carbonyl}amino)-5-fluoro-4-oxopentanoic acid (Iaa12);

(39) 3-({[3-(4-cyclopentyl-2-pyridinyl)-5-ethyl-4,5-dihydro-5-isoxazolyl]carbonyl}amino)-5-fluoro-4-oxopentanoic acid (Iaa13);

(40) 3-({[(5R)-3-(4-cyclopentyl-2-pyridinyl)-5-isopropyl-4,5-dihydro-5-isoxazolyl]carbonyl}amino)-5-fluoro-4-oxopentanoic acid (Iaa14);

(41) 3-({[3-(4-cyclohexyl-2-pyridinyl)-5-ethyl-4,5-dihydro-5-isoxazolyl]carbonyl}amino)-5-fluoro-4-oxopentanoic acid (Iaa15);

(42) 3-({[5-ethyl-3-(5,6,7,8-tetrahydro-1-isoquinolinyl)-4,5-dihydro-5-isoxazolyl]carbonyl}amino)-5-fluoro-4-oxopentanoic acid (Iaa16);

(43) 5-fluoro-3-({[5-isopropyl-3-(4-phenyl-2-pyridinyl)-4,5-dihydro-5-isoxazolyl]carbonyl}amino)-4-oxopentanoic acid (Iaa17);

(44) (3S)-5-[(diphenylphosphoryl)oxy]-3-({[(5R)-5-isopropyl-3'-(1-isoquinolinyl)-4,5-dihydro-5-isoxazolyl]carbonyl}amino)-4-oxopentanoic acid (Iaa18);

(45) (3S)-3-({[(5R)-5-isopropyl-3-(1-isoquinolinyl)-4,5-dihydro-5-isoxazolyl]carbonyl}amino)-4-oxo-5-{1-phenyl-3'-(trifluoromethyl)-1H-pyrazol-5-yl]oxy}pentanoic acid (Iaa19);

(46) (3S)-5-[(4-benzyl-5-oxo-2,5-dihydro-3-furanyl)oxy-3-({[(5R)-5-isopropyl-3-(1-isoquinolinyl)-4,5-dihydro-5-isoxazolyl]carbonyl}amino)-4-oxopentanoic acid (Iaa20);

(47) (3S)-5-(isobutyryloxy)-3-({[(5R)-5-isopropyl-3-(1-isoquinolinyl)-4,5-dihydro-5-isoxazolyl]carbonyl}amino)-4-oxopentanoic acid (Iaa21);

(48) (3S)-3-({[(5R)-5-isopropyl-3-(1-isoquinolinyl)-4,5-dihydro-5-isoxazolyl]carbonyl}amino)-4-oxo-5-hexenoic acid (Iaa22);

(49) (3S)-3-({[(5R)-5-isopropyl-3-(1-isoquinolinyl)-4,5-dihydro-5-isoxazolyl]carbonyl}amino)-4-oxo-5-(2-pyridinyloxy)pentanoic acid (Iaa23);

(50) (3S)-3-({[5-ethyl-3-(2-isopropylphenyl)-4,5-dihydro-5-isoxazolyl]carbonyl}amino)-4-oxo-5-(2-pyridinyloxy)pentanoic acid (Iaa24);

(51) 2-{[(3S)-4-carboxy-3-({[(5R)-5-isopropyl-3'-(1-isoquinolinyl)-4,5-dihydro-5-isoxazolyl]carbonyl}amino)-2-oxobutyl]oxy}-1-methylpyridinium trifluoromethanesulfonate (Iaa25);

(52) 2-{[(3S)-4-carboxy-3-({[5-ethyl-3-(2-isopropylphenyl)-4,5-dihydro-5-isoxazolyl]carbonyl}amino)-2-oxobutyl]oxy}-1-methylpyridinium trifluoromethanesulfonate (Iaa26);

(53) 3-({[3-(5-chloro-1-methyl-1H-indol-2-yl)-5-isopropyl-4,5-dihydro-5-isoxazolyl]carbonyl}amino)-5-fluoro-4-oxopentanoic acid (Iaa27);

(54) 3-({[3-(1,5-dimethyl-1H-indol-2-yl)-5-isopropyl-4,5-dihydro-5-isoxazolyl]carbonyl}amino)-5-fluoro-4-oxopentanoic acid (Iaa28); and

(55) (3S)-5-fluoro-3-({[(5R)-5-isopropyl-3-(1-isoquinolinyl)-4,5-dihydro-5-isoxazolyl]carbonyl}amino)-4-oxopentanoic acid (Iii-1).

8. The compound according to claim 1 which is 5-fluoro-3-({[(5R)-5-isopropyl-3-(1-isoquinolinyl)-4,5-dihydro-5-isoxazolyl]carbonyl}amino)-4-oxopentanoic acid (Iii).

9. A compound of the following formula (1a):

(1a)

in which

A, B, R, R¹, R², and X are defined as described in claim 1.

10. The compound according to claim 9 which is (3S)-5-fluoro-3-({[(5R)-5-isopropyl-3'-(1-isoquinolinyl)-4,5-dihydro-5-isoxazolyl]carbonyl}amino)-4-oxopentanoic acid (Iii-1).

11. A process for preparing the compound (Iii-1) as defined in claim 10, which comprises the steps of dissolving a mixture of (3S)-5-fluoro-3-({[(5R)-5-isopropyl-3-(1-isoquinolinyl)-4,5-dihydro-5-isoxazolyl]carbonyl}amino)-4-oxopentanoic acid and (3R)-5-fluoro-3-({[(5R)-5-isopropyl-3-(-isoquinolinyl)-4,5-dihydro-5-isoxazolyl]carbonyl}amino)-4-oxopentanoic acid in methyl t-butyl ether, adding a small amount of crystalline (3S)-5-fluoro-3-({[(5R)-5-isopropyl-3-(1-isoquinolinyl)-4,5-dihydro-5-isoxazolyl]carbonyl}amino)-4-oxopentanoic acid as a seed material to give a crystal, and recrystallizing this crystal from ethyl acetate/n-hexane solvent system.

12. A therapeutic composition comprising the caspase inhibitor compound of formula (1), salt, or stereoisomer thereof as defined in claim 1 as an active ingredient together with the pharmaceutically acceptable carrier.

13. The composition according to claim 12 for the treatment of acute hepatitis or liver cirrhosis.

14. The composition according to claim 12 for the treatment of rheumatic arthritis.

15. The composition according to claim 12 which is formulated as an oral preparation, an injection, or a patch.

16. The composition according to claim 12 comprising the compound (Iii) as defined in claim 8 as an active ingredient.

17. The composition according to claim 12 comprising the compound (Iii-1) as defined in claim 10 as an active ingredient.

18. A process for preparing the therapeutic composition as defined in claim 12, comprising admixing the caspase inhibitor compound of formula (1), salt, or stereoisomer thereof as defined in claim 1 with pharmaceutically acceptable carrier.

19. A method for treating apoptosis, comprising administering an effective amount of the caspase inhibitor compound of formula (1), salt, or stereoisomer thereof as defined in claim 1 to a patient suffering from apoptosis.

20. The method according to claim 19, for the treatment of acute hepatitis or liver cirrhosis.

21. The method according to claim 19, for the treatment of rheumatic arthritis.

* * * * *